US007360539B2

(12) United States Patent
Gurneé et al.

(10) Patent No.: US 7,360,539 B2

(45) Date of Patent: *Apr. 22, 2008

(54) HYPERBARIC OXYGEN THERAPY SYSTEM CONTROLS

(75) Inventors: William T. Gurneé, LaJolla, CA (US); Juan Jose Garay, San Diego, CA (US)

(73) Assignee: Hyperbaric Technology, Inc., National City, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 11/101,698

(22) Filed: Apr. 8, 2005

(65) Prior Publication Data

US 2005/0178387 A1 Aug. 18, 2005

Related U.S. Application Data

(62) Division of application No. 10/087,042, filed on Feb. 28, 2002.

(60) Provisional application No. 60/272,416, filed on Feb. 28, 2001.

(51) Int. Cl.
*A61M 11/00* (2006.01)

(52) U.S. Cl. ............................ 128/205.26; 128/204.18

(58) Field of Classification Search ........... 128/202.12, 128/204.22, 205.26, 204.18, 205.24; 417/312
See application file for complete search history.

(56) References Cited

U.S. PATENT DOCUMENTS

| | | | | |
|---|---|---|---|---|
| 826,029 | A | 7/1906 | Harper | |
| 1,224,180 | A | 5/1917 | Lake | |
| 2,160,326 | A | 5/1939 | Carbonara | |
| 2,299,109 | A | 10/1942 | Rand | |
| 2,723,660 | A | 11/1955 | Greenberg | |
| 2,920,622 | A | 1/1960 | Steel | |
| 2,998,009 | A | 8/1961 | Holm et al. | |
| 3,405,629 | A | 10/1968 | Krasberg | |
| 3,587,574 | A | 6/1971 | Mercer et al. | |
| 3,902,488 | A | 9/1975 | Sheppard | |
| 4,106,504 | A | 8/1978 | York | |
| 4,164,172 | A | 8/1979 | Anderten | |
| 4,362,154 | A | 12/1982 | Le Masson | |
| 4,602,653 | A | 7/1986 | Ruiz-Vela et al. | |
| 4,633,859 | A | 1/1987 | Reneau | |
| 4,974,829 | A | 12/1990 | Gamow et al. | |
| 5,101,819 | A * | 4/1992 | Lane | 128/204.18 |
| 5,188,099 | A | 2/1993 | Todeschini et al. | |

(Continued)

*Primary Examiner*—Steven O. Douglas
(74) *Attorney, Agent, or Firm*—Panitch Schwarze Belisario & Nadel LLP

(57) ABSTRACT

A hyperbaric oxygen therapy system includes a pressure vessel containing a gas, an oxygen concentration measurement apparatus for monitoring the concentration of oxygen in the gas, an environmental control apparatus for controlling the temperature of the gas in the vessel, and a pressure/ventilation control apparatus for controlling the pressure of the gas in the vessel. The pressure vessel is capable of accommodating a patient. The oxygen concentration measurement apparatus includes an oxygen concentration analyzer and a plurality of gas lines connecting the oxygen analyzer to the pressure vessel. The pressure/ventilation control apparatus includes a pressure controlling valve, a pressure sensor, a ventilation valve, and a controller having a programmable pressure profile. The environmental control apparatus includes a scrubber, a heat exchanger and a blower located within the pressure vessel. A compressor for the system includes a compressor silencer. An airlock providing access to the pressure vessel includes a safety mechanism.

6 Claims, 16 Drawing Sheets

U.S. PATENT DOCUMENTS 5,398,678 A 3/1995 Gamow
5,421,340 A 6/1995 Stanga et al.
5,503,143 A 4/1996 Marion
5,765,555 A * 6/1998 Garrett .................. 128/205.26

* cited by examiner

HYPERBARIC OXYGEN THERAPY SYSTEM CONTROLS

CROSS-REFERENCE TO RELATED APPLICATIONS

This application is a divisional application of U.S. patent application Ser. No. 10/087,042 filed Feb. 28, 2002 entitled "Hyperbaric Oxygen Therapy System Controls." This application claims the benefit of U.S. Provisional Application 60/272,416, filed Feb. 28, 2001, entitled "Hyperbaric Oxygen Therapy System," which is incorporated herein by reference in its entirety.

BACKGROUND OF THE INVENTION

The present invention relates generally to hyperbaric chambers and more particularly to a hyperbaric chamber and associated control systems for delivering hyperbaric oxygen therapy to one or more persons.

Hyperbaric oxygen therapy is indicated for treating many medical conditions and for training regimens such as the treatment of severe burns, peripheral vascular disease, carbon monoxide poisoning, decompression illness and the like. Such therapy is generally administered in a hyperbaric pressure vessel. In the case of sports injuries or training, athletes can benefit from exercising within a hyperbaric pressure vessel.

Typically, hyperbaric therapy requires that the pressure in the vessel be varied at a predetermined rate from atmospheric up to a treatment level which may be as high as three atmospheres. The pressure is then maintained at a substantially constant level for a predetermined time or "soaking interval". Following the soaking interval, the pressure is reduced to atmospheric at a predetermined rate. During the treatment cycle, the temperature in the vessel is required to be controlled and the air is required to be circulated and cleansed of the carbon dioxide exhaled by the patient undergoing therapy. A means for passing articles into and out of the chamber while the chamber is pressurized, is also required.

Current hyperbaric chambers suffer from a number of deficiencies which cause discomfort to the patient, require excessive human intervention to monitor and control the treatment cycle and present safety hazards. Typically, the environment in the vessel is excessively noisy due to the noise generated by the compressor required to elevate the pressure in the vessel and due to blowers required to circulate the air in the vessel. Further, the pressure in typical hyperbaric chambers is manually controlled requiring constant attention by an operator. Further, airlocks for passing articles into and out of the pressure vessel may be operated in a manner which could cause injury by allowing the door to the airlock to be opened while the airlock is pressurized.

Accordingly, there is a need for a hyperbaric oxygen therapy system which: (1) provides automatic control of the pressure, ventilation and temperature of the gas in the pressure vessel, (2) reduces the noise in the pressure vessel and (3) provides a means for passing articles into and out of the pressure vessel which cannot present a hazardous condition to the operator.

BRIEF SUMMARY OF THE INVENTION

Briefly stated, the present invention comprises a hyperbaric oxygen therapy system including a pressure vessel containing a gas, an oxygen concentration measurement apparatus for monitoring the concentration of oxygen in the gas, an environmental control apparatus for controlling the temperature of the gas in the vessel, and a pressure/ventilation control apparatus for controlling the pressure of the gas in the vessel. The pressure vessel is capable of accommodating a patient.

The present invention further comprises a hyperbaric oxygen therapy system that includes an oxygen concentration measurement apparatus, wherein the oxygen concentration measurement apparatus includes an oxygen concentration analyzer providing an output representative of a concentration of oxygen in the gas. The oxygen concentration measurement apparatus also includes a plurality of gas lines connecting the oxygen analyzer to the pressure vessel for conducting the gas from an interior of the pressure vessel to the oxygen analyzer. Each gas line has a port in a separate location of a wall of the pressure vessel for receiving the gas in the pressure vessel. The oxygen concentration measurement apparatus also includes a sample valve located in each gas line for opening and closing the port and a controller for actuating the sample valve to open and close the port according to a predetermined schedule. The oxygen concentration measurement apparatus may include a vent valve in fluid communication with the oxygen analyzer for venting the gas from the analyzer subsequent to closing each sample valve.

The present invention further comprises a hyperbaric oxygen therapy system wherein an environmental control apparatus includes a scrubber, a heat exchanger and a blower located within the pressure vessel, each of which is in fluid communication with the gas. The environmental control apparatus also includes a heat pump in fluid communication with the heat exchanger by a conduit having an exchange fluid therein. The environmental control apparatus further includes a temperature sensor in fluid communication with the gas in the vessel which provides an output representative of a temperature of the gas and a temperature controller having an adjustable set point which receives the output of the temperature sensor and provides a control signal to the heat pump for adjusting the temperature of the exchange fluid to thereby maintain the temperature of the gas within a predetermined range of the set point. The scrubber may contain a carbon dioxide adsorbing packing material for removing carbon dioxide from the gas. The blower may be an injection blower and may operate by receiving gas from a source of pressurized gas.

The present invention further comprises a hyperbaric oxygen therapy system wherein a pressure/ventilation control apparatus includes a pressure controlling valve for regulating a flow of pressurized gas into the pressure vessel, a pressure sensor in fluid communication with the gas in the pressurized vessel that outputs a signal representative of a pressure of the gas within the pressure vessel, a ventilation valve that regulates a gas flow out of the pressure vessel, and a controller having a programmable pressure profile. The controller controls the pressure controlling valve to maintain a pressure of the gas in the pressurized vessel to within a predetermined range around the programmed pressure profile and controls the ventilation valve to adjust the ventilation flow rate according to the pressure profile.

The present invention further comprises a hyperbaric oxygen therapy system that has a compressor. The compressor includes an intake, an outtake, and at least one compressor silencer connected to at least one of the intake and the outtake. The compressor silencer includes a silencer housing including an elongate body having an inlet end and an outlet end, an inlet cap secured to the inlet end of the body, an outlet cap secured to the outlet end of the body. The silencer may optionally include a porous packing material. The packing material is located within the elongate body and fills at least part of the volume between the inlet end and the outlet end of the body. The packing material is supported by the inlet cap and the outlet cap.

The present invention further comprises a method for performing hyperbaric oxygen therapy in a pressurized vessel containing a gas including the steps of setting a pressure profile, setting a treatment temperature of the gas in the pressure vessel, setting a first ventilation rate, performing a treatment cycle in accordance with the pressure profile wherein the pressure is first changed from a first pressure to a second pressure, after which the pressure of the gas is maintained at a substantially steady pressure during which time the gas in the vessel is vented from the vessel at the first ventilation rate, after which the pressure of the gas is decreased and the gas in the vessel is vented at a second rate and wherein during the treatment cycle, the oxygen concentration in the vessel is monitored at a plurality of locations, carbon dioxide is removed from the gas and the temperature of the gas is maintained at the treatment temperature.

The present invention further comprises a safety mechanism for an airlock providing access to a pressure vessel. The airlock includes an exterior door mounted in an exterior door frame, an interior door mounted in an interior door frame and a transfer chamber connecting the exterior door frame and the interior door frame. The safety mechanism also includes a first selector located in the exterior door frame moveable between a first position and a second position and a second selector located in the exterior door frame. The second selector is moveable from a first position to a second position only when the first selector is in the second position. The first selector is moveable from the second position to the first position only when the second selector is in the first position.

The present invention further comprises method for enabling transfer of an object from an interior of an airlock to a pressure vessel attached to the airlock and ensuring that an exterior door of the airlock cannot be opened when the interior of the airlock is pressurized. The method includes the steps of actuating a first selector from a first position to a second position whereby the first selector causes the exterior door to be locked and sealed, thereafter actuating a second selector from a first position to a second position thereby closing a vent from the interior of the airlock to the atmosphere, and thereafter actuating a third selector from a first position to a second position thereby opening a vent between the interior of the airlock and the pressure vessel thereby enabling a door between the interior of the pressure vessel and the interior of the airlock to be opened.

The present invention further comprises a method for enabling transfer of an object from an interior of an airlock attached to a pressure vessel to the atmosphere and ensuring that an exterior door of the airlock opening to the atmosphere cannot be opened when the interior of the airlock is pressurized. The method includes the steps of closing a door between the interior of the airlock and the pressure vessel, thereafter actuating a third selector from a second position to a first position thereby closing a vent between the interior of the airlock and the pressure vessel, thereafter actuating a second selector from a second position to a first position thereby opening a vent from the interior of the airlock to the atmosphere, and thereafter actuating a first selector from a second position to a first position whereby the first selector causes the exterior door to be unlocked and unsealed.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 11B is a front exploded view of a safety mechanism shown in FIG. 11A showing the first, second and third selectors in the second position;

DETAILED DESCRIPTION OF THE INVENTION

Figure 1:
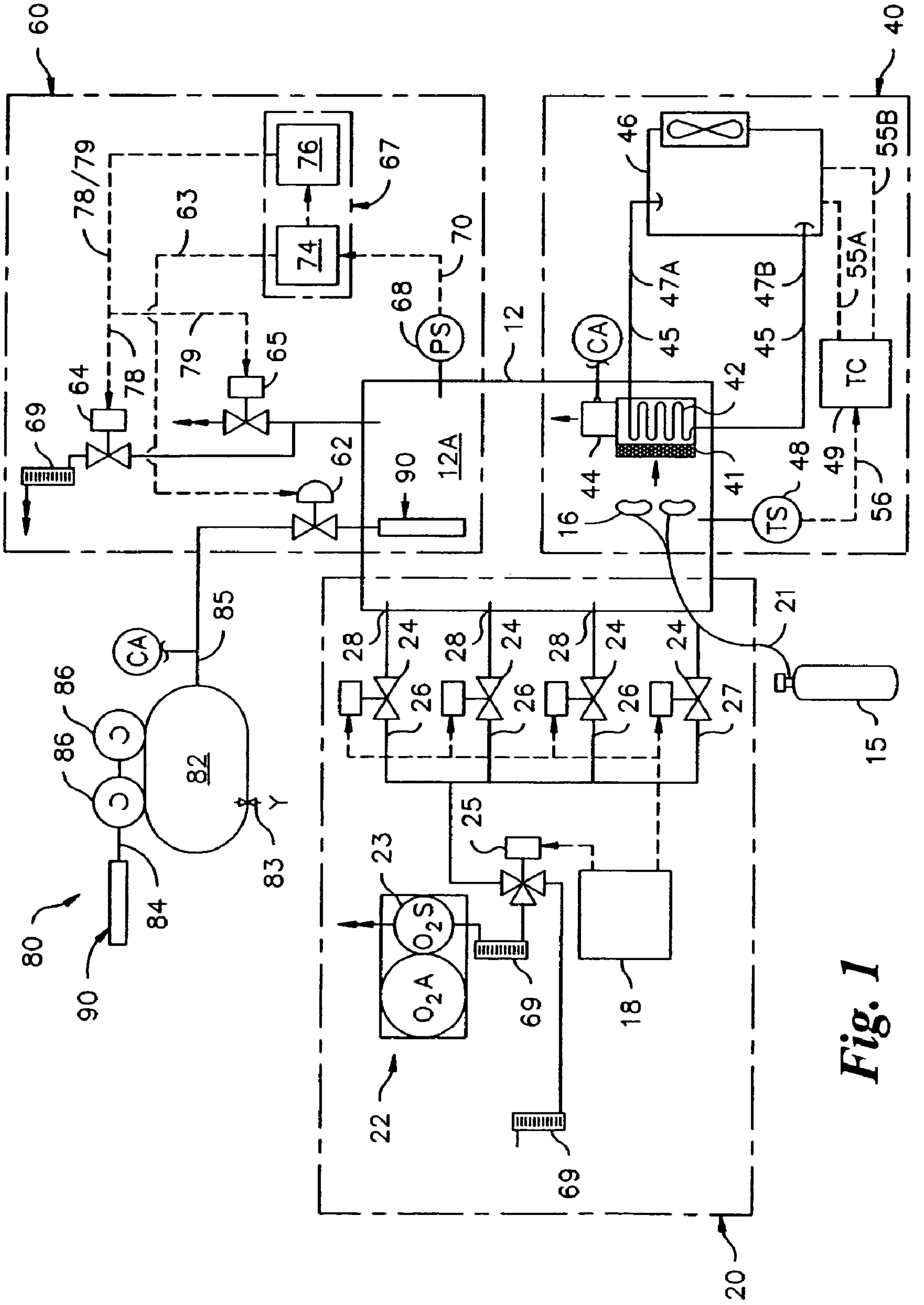
FIG. 1 is a schematic diagram of a preferred embodiment of a hyperbaric oxygen therapy system.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the object discussed and designated parts thereof. The terminology includes the words above specifically mentioned, derivatives thereof and words of similar import. Additionally, the word "a" as used in the claims and in the corresponding portions of the specification, means "one or more than one."

In the drawings, like numerals are used to indicate like elements throughout. Referring to the drawings in detail, there is shown in FIG. 1 a schematic diagram of a hyperbaric oxygen therapy system 10 in accordance with a preferred embodiment. The hyperbaric oxygen therapy system 10 includes a pressure vessel 12 containing a gas (not shown), an oxygen concentration measurement apparatus 20 for monitoring the concentration of oxygen in the pressure vessel 12, an environmental control apparatus 40 for controlling the temperature of the gas in the pressure vessel 12, and a pressure/ventilation control apparatus 60 for controlling the pressure of the gas in the vessel. The pressure vessel 12 is capable of accommodating a patient. The hyperbaric oxygen therapy system 10 also includes at least one bottle of breathing gas 15, a breathing line 21, and breathing masks 16.

Figure 2A:
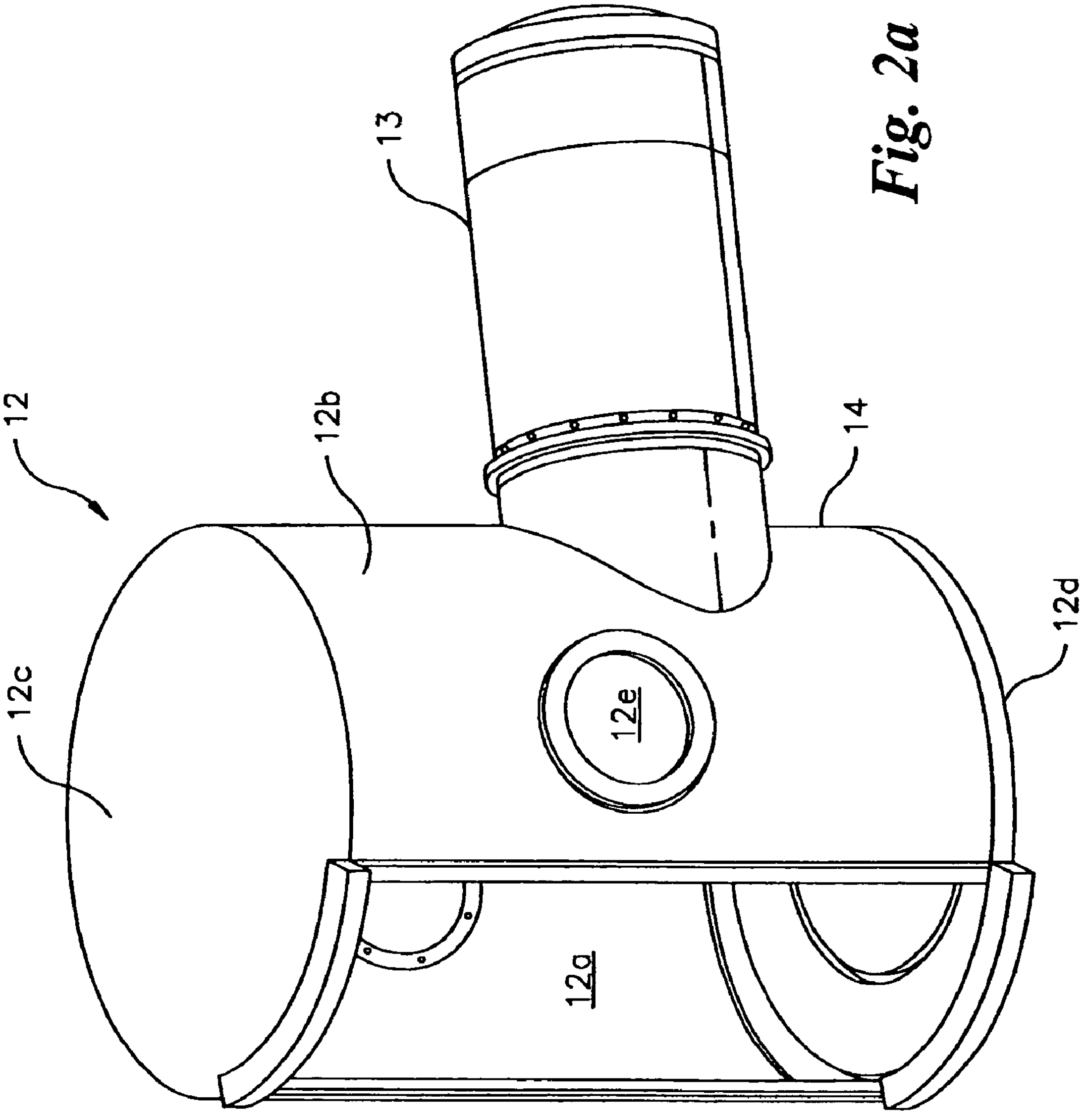
FIG. 2A is a perspective view of a vertically oriented pressure vessel in accordance with the preferred embodiment.
Figure 2B:
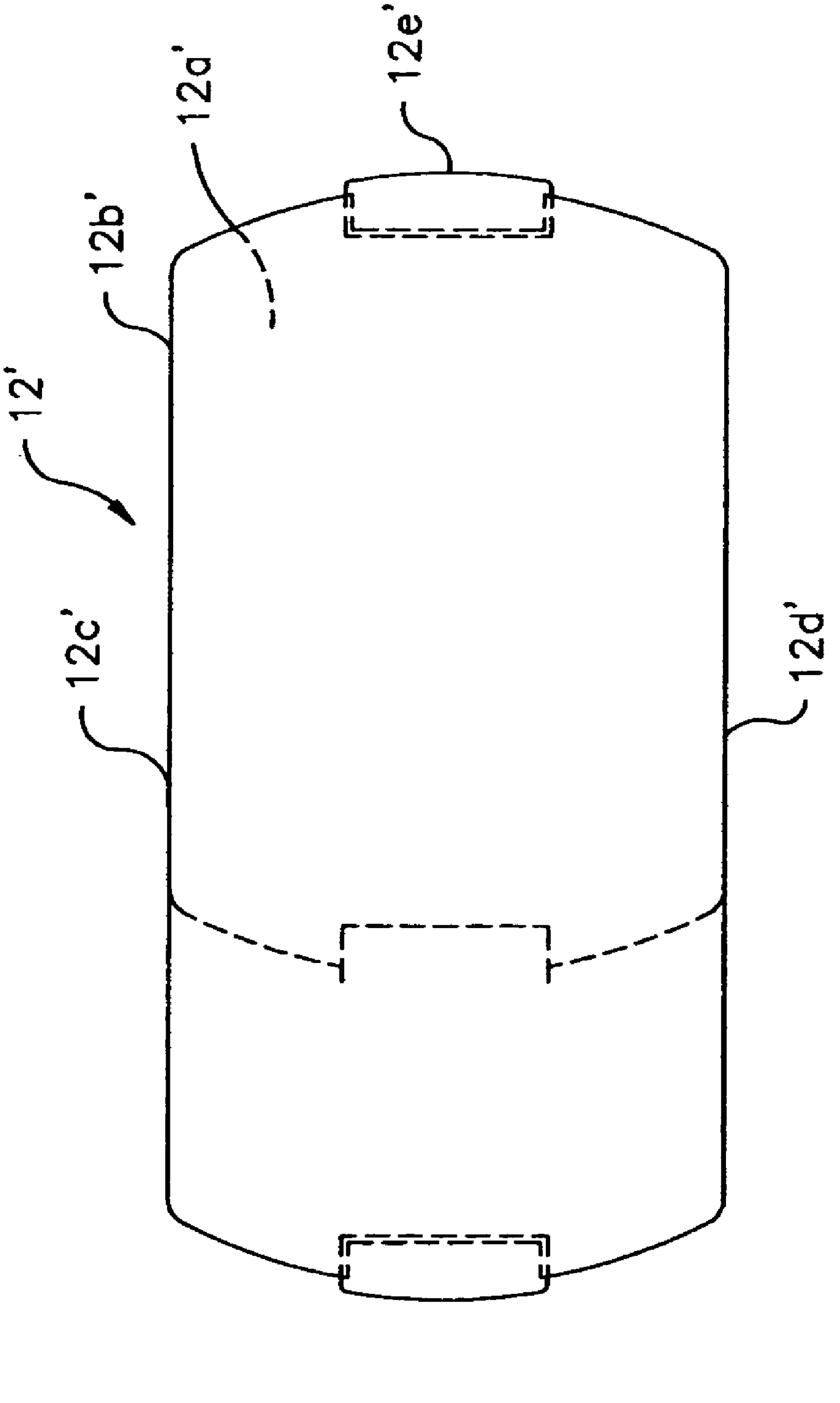
FIG. 2B is a perspective view of a pressure vessel in a horizontal orientation according to an alternative embodiment.

FIG. 2A is a perspective view of the preferred embodiment of the pressure vessel 12. The pressure vessel 12 has an interior 12*a*, an exterior 12*b*, a top 12*c*, a bottom 12*d* and a window or windows 12*e*. In a preferred embodiment, the pressure vessel 12 is a vertically-oriented, generally cylindrically-shaped structure. The vertically-oriented pressure vessel 12 may include a generally horizontal extension chamber 13 within which a user or multiple users, either human or animal (not shown), receive hyperbaric treatment for a multitude of illnesses, impairments, therapies, or for athletic training. The pressure vessel 12 need not include the horizontal extension chamber 13. Users may receive, at hyperbaric pressures (i.e., pressure equal to or greater than 1 atmosphere) treatment of up to one hundred percent hyperbaric oxygen while inside the pressure vessel 12. The pressure vessel 12 is preferably built to American Society of Mechanical Engineers ("ASME") guidelines to withstand the pressure differential between the environments within and outside the pressure vessel 12. Accordingly, except where noted below, the pressure vessel 12 is preferably made from steel. To improve user comfort and permit users of the pressure vessel 12 to enter or remain in the pressure vessel 12 in the upright position, the height of the pressure vessel 12 is preferably at least that required to permit such standing position of the user. In a preferred embodiment, the diameter of the pressure vessel 12 is such as to permit multiple users to stand or sit in the pressure vessel 12 at one time. The present invention is not limited to any particular diameter pressure vessel 12. Larger diameters are preferred for treating a larger number of patients. In an alternate embodiment of the pressure vessel, shown in FIG. 2B, a pressure vessel 12' has an interior 12*a*', an exterior 12*b*', a top 12*c*', a bottom 12*d*' and a window 12*e*'. The pressure vessel 12' is a generally horizontally-oriented, cylindrically-shaped structure. It should be noted, however, that the shape and orientation of the pressure vessel 12 is not critical to the present invention, and that the pressure vessel 12 could be other shapes and orientations without departing from the scope of the present invention.

Referring to FIG. 1, the oxygen concentration measurement apparatus 20 includes an oxygen concentration analyzer 22 providing an output representative of a concentration of oxygen in the gas. The oxygen concentration measurement apparatus 20 also includes a plurality of gas lines 26 connecting the oxygen analyzer 22 to the pressure vessel 12 for conducting the gas from the interior 12*a* of the pressure vessel 12 to the oxygen analyzer 22. Each gas line 26 has a port 28 in a separate location of a wall 14 of the pressure vessel 12 for receiving the gas in the pressure vessel 12. The oxygen concentration measurement apparatus 20 also includes a sample valve 24 located in each gas line 26 for opening and closing the port 28 in each gas line 26 and a controller 18 for actuating the sample valve 24 to open and close the port 28 according to a predetermined schedule. One sample valve 24 is connected to the breathing line 16 by an additional gas line 27. Preferably, there are three gas lines 26, but there could be more or less. The oxygen concentration measurement apparatus 20 preferably includes a vent valve 25 in fluid communication with the oxygen analyzer 22 for venting the gas from the analyzer 22 subsequent to closing each sample valve 24. The oxygen concentration measurement apparatus 20 preferably includes an alarm (FIG. 3), described in detail below, for signaling or annunciating when the measured concentration of oxygen is outside a predetermined range.

The oxygen concentration measurement apparatus 20 also includes an oxygen sensor 23. The oxygen sensor 23 is preferably a depleting-electrolyte type (via galvanic reaction) sensor that has a usable life of approximately six months to one year depending upon the volume of free oxygen passed over the oxygen sensor 23. Preferably, the oxygen concentration analyzer 22 incorporates the oxygen sensor 23. However, the oxygen sensor 23 may be remotely mounted and electrically connected to the analyzer via an oxygen sensor cable 36 (FIG. 3).

Figure 3:
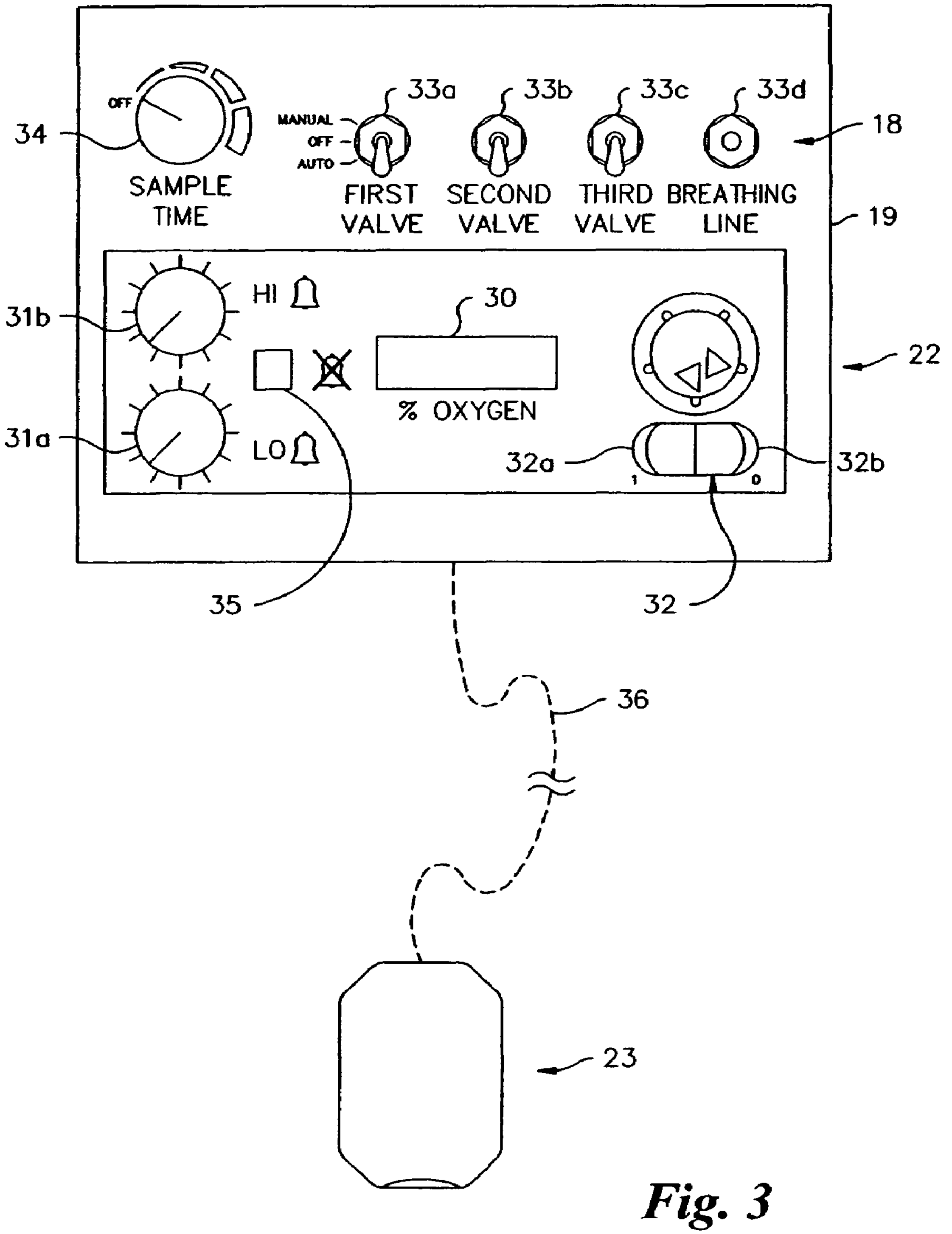
FIG. 3 is a front view of an oxygen analyzer including an oxygen sensor, and a controller for controlling the samples of oxygen provided to the oxygen analyzer in accordance with the preferred embodiment.

Referring to FIG. 3, the controller 18 includes a mounting plate 19, manual-off-auto switches 33*a*, 33*b*, 33*c*, 33*d* for each of the sample valves 24 and a sample time switch 34. Preferably at least an indicating portion of the oxygen concentration analyzer 22 is mounted in the mounting plate 19 of the controller 18, but need not be. The controller 18 also includes a printed circuit board (PCB) 17 (FIG. 4) for controlling the sample valves 24 and the vent valve 25.

The oxygen concentration analyzer 22 preferably has an oxygen indicator 30, a low alarm limit 31*a*, a high alarm limit 31*b*, an on/off switch 32 having an on-position 32*a* and an off-position 32*b*, and an alarm indicator/silence pushbutton 35. The oxygen indicator 30 is preferably a liquid crystal display (LCD), but the oxygen indicator 30 may be a seven segment (7-segment) light emitting diode (LED) indicator, an analog indictor or some other indicator capable of displaying oxygen concentration without departing from the present invention.

High and low alarm trip-points (software) may be set using the high and low alarm limits 31*a*, 31*b* in a range of approximately 18% to 102% of oxygen concentration. In the event of a violation of the alarm limits 31*a*, 31*b*, the oxygen concentration analyzer 22 provides both an audible and a visual alarm signal. The audible alarm is annunciated via a speaker or siren (not shown). The visual alarm will be indicated by the alarm indicator/silence pushbutton 35. Under such conditions, an operator can "mute" or temporarily silence the audible alarm for a delay time of approximately sixty seconds to allow corrective action to be taken by momentarily pushing the alarm indicator/silence pushbutton 35. If the alarm condition is not rectified within the delay time, the audible alarm will be automatically reinstated. The audible alarm signals are tonally matched to the type of threshold violations (i.e. low alarm violations are signaled via a lower pitched audible signal, while high alarm violations are signaled via a higher pitched audible signal). Preferably, the analyzer 22 will alarm at any oxygen concentration below 18% regardless of the low and high alarm limits 31*a,* 31*b*. Preferably, the oxygen concentration analyzer 20 is a Teledyne TED 191 and the associated oxygen sensor is a Teledyne T-7 galvanic-type Micro-Fuel Cell. However, oxygen concentration analyzers 22 and associated oxygen sensors 23 are generally well known in the art, and as such, a commercially available oxygen concentration analyzer, an oxygen analyzer or an oxygen measurement device may be utilized in combination with the controller 18 without departing from the spirit and scope of the present invention.

Figure 4:
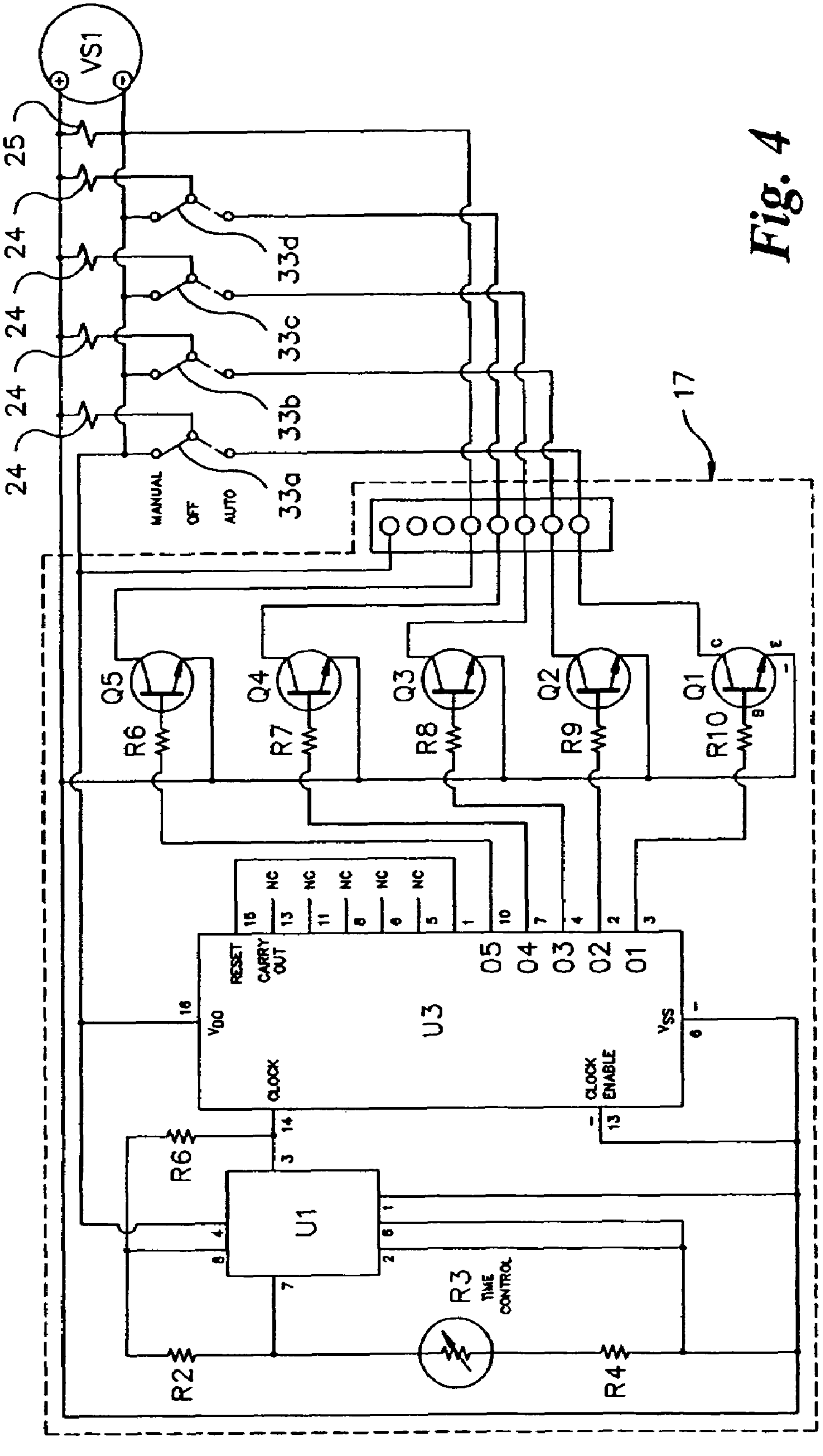
FIG. 4 is an electrical schematic diagram of the controller shown in FIG. 3.

Referring to FIG. 4, the PCB 17 includes a timer integrated circuit (IC) U1, a sequencer IC U2, a potentiometer R3 actuated by the sample time switch 34, drive transistors Q1-Q5, and appropriate biasing resistors R2, R4-R10. The controller 18 may include a voltage source VS1, or the voltage source VS1 may be a separately located device. The potentiometer provides an adjustable voltage input to the time IC U1 to adjust a timer preset. The timer IC U1 provides an output to an input of the sequencer IC U2 based upon the timer preset counting up and/or resetting. The sequencer IC U2 preferably energizes outputs O1-O4 sequentially and independently in order to energize or gate transistors Q1-Q4, respectively. The sequencer IC U2 preferably energizes output O5 independently in order to energize transistor Q5 subsequent to energizing each of the outputs O1-O4. The sequencer IC U2 may energize the outputs in other orders or for different times without departing from the scope of the present invention. If the manual-off-auto switch 33*a*-33*d* is in an auto-position and the respective transistor Q1-Q4 is energized, the sample valve 24 associated with the particular manual-off-auto switch 33*a*-33*d* will be energized. If the manual-off-auto switch 33*a*-33*d* is in an off-position, the sample valve 24 associated with the particular manual-off-auto switch 33*a*-33*d* cannot be energized. If the manual-off-auto switch 33*a*-33*d* is in a manual-position, the sample valve 24 associated with the particular manual-off-auto switch 33*a*-33*d* is energized regardless of the respective output O1-O4 of the sequencer IC U2. While in the presently preferred embodiment the PCB 17 includes the timer IC U1 and the sequencer IC U2, the PCB 17 could alternatively be an application specific integrated circuit (ASIC), a programmable array logic (PAL), a microcontroller, and the like without departing from the broad inventive scope of the present invention. It is also contemplated that the PCB 17 could be a commercially available programmable controller or programmable logic controller (PLC) or a personal computer with a digital input/output (I/O) expansion card.

Referring again to FIG. 1, the environmental control apparatus 40 includes a scrubber 41 for removing undesirable gases and impurities from the gas in the vessel, a heat exchanger 42 and a blower 44 located within the interior 12*a* of the pressure vessel 12, each of which is in fluid communication with the gas. The environmental control apparatus 40 also includes a heat pump 46. Preferably, the heat exchanger 42 is in fluid communication with the heat pump by a first conduit 47*a* and a second conduit 47*b* both having an exchange fluid 45 therein. Preferably, the exchange fluid 45 is a mixture of approximately 30% ethylene glycol and approximately 70% water. The exchange fluid 45, however, can be other ratios of ethylene glycol and water or can be another fluid or fluid combination without departing from the present invention.

The heat pump 46 heats, cools or takes no action on the exchange fluid 45 as commanded to do so. Heat pumps are generally well known in the art; therefore, the heat pump 46 will not be discussed in greater detail herein.

Figure 7:
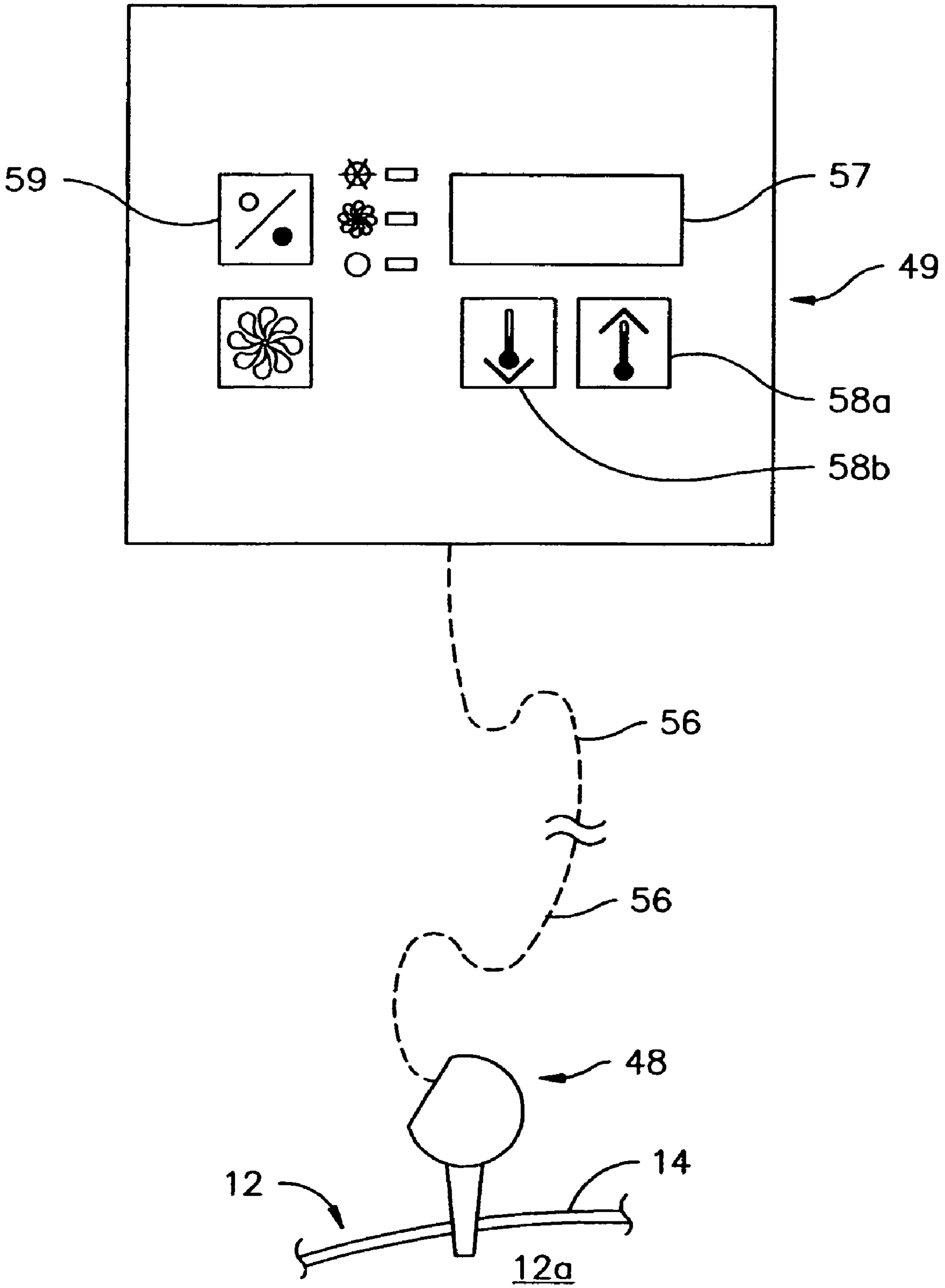
FIG. 7 is a front view of a temperature controller and a temperature sensor in accordance with the preferred embodiment.
Figure 8B:
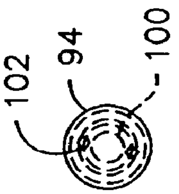
FIG. 8B is an end view of the muffler shown in FIG. 8A.
Figure 8C:
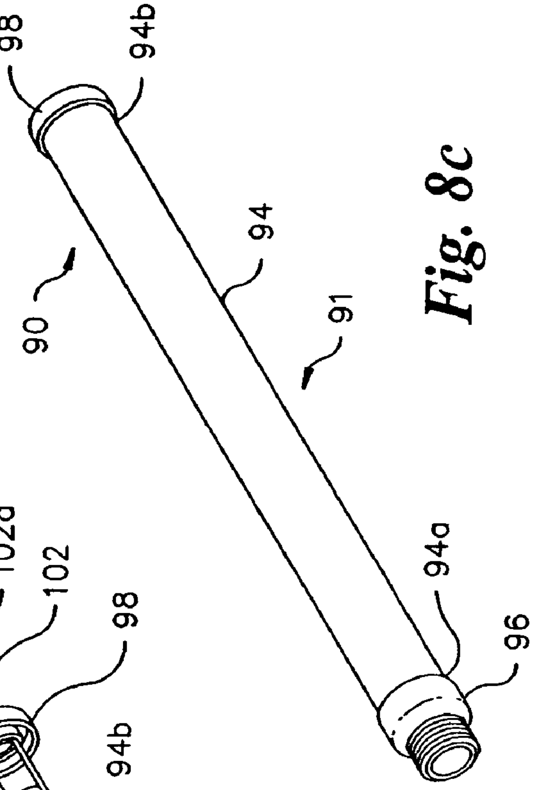
FIG. 8C is a perspective view of the muffler shown in FIG. 8A.
Figure 8A:
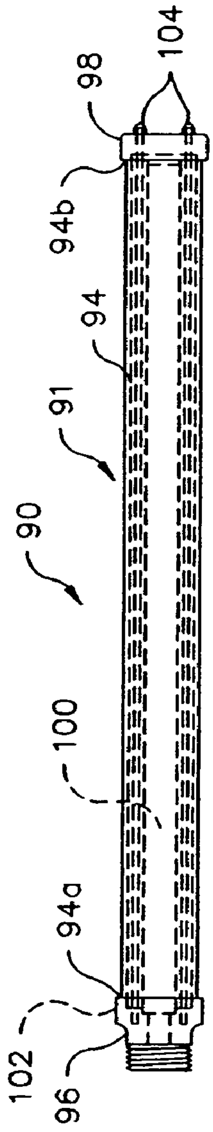
FIG. 8A is a side elevational view of a muffler in accordance with the preferred embodiment.
Figure 8D:
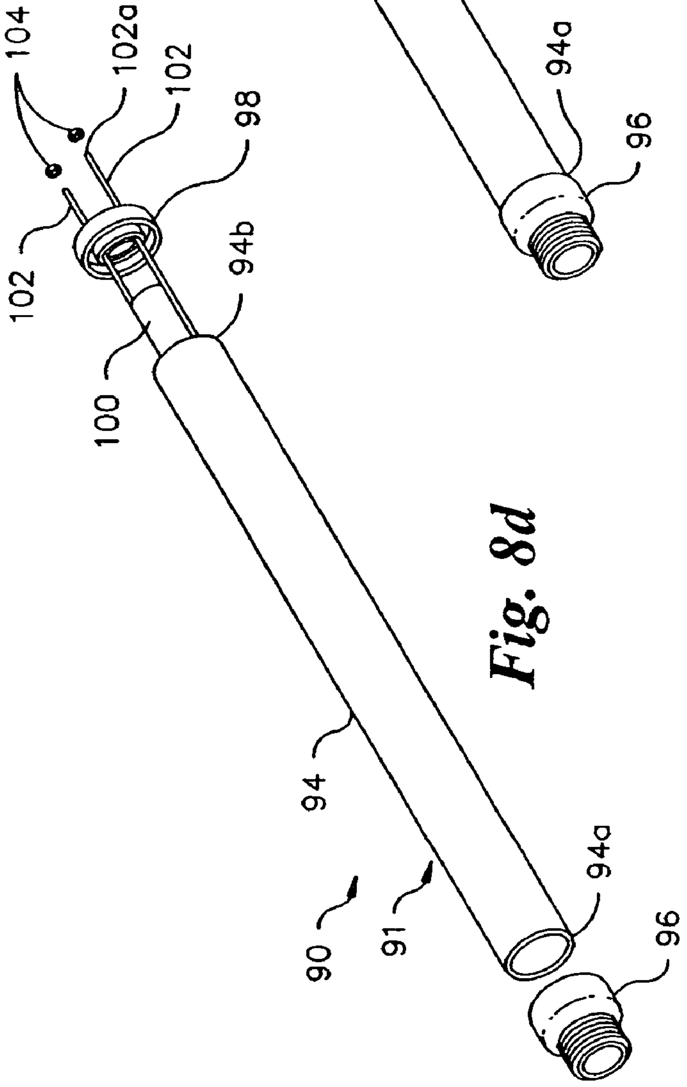
FIG. 8D is an exploded perspective view of the muffler shown in FIG. 8A.

Referring to FIG. 7, the environmental control apparatus 40 further includes a temperature sensor 48 which provides an output representative of a temperature of the gas in the pressure vessel and a temperature controller 49 having an adjustable set point which receives the output of the temperature sensor 48 and provides a control signal or signals to the heat pump 46 for adjusting the temperature of the exchange fluid to thereby maintain the temperature of the gas within a predetermined range of the set point. The temperature sensor 48 is preferably a silicone-based thermistor. However, the temperature sensor 48 could be another device such as a thermocouple, a resistive thermal device (RTD) and the like. The temperature sensor 48 or a sensing portion thereof is preferably in fluid communication with the gas in the interior 12*a* of the pressure vessel 12. The output of the temperature sensor 48 is preferably an electrical signal transmitted by a temperature signal cable 56.

The temperature controller 49 preferably includes a temperature setpoint indicator 57, an increase setpoint pushbutton 58*a,* a decrease setpoint pushbutton 58*b* and a temperature controller on/off pushbutton 59. The temperature controller 49 is powered from a power source (not shown) of approximately 49 VAC to 230 VAC at approximately 50-60 Hertz (Hz). The increase setpoint pushbutton 58*a* is used to increase the setpoint of the temperature controller 49 as displayed on the temperature setpoint indicator 57. Conversely, the decrease setpoint pushbutton 58*b* is used to decrease the setpoint of the temperature controller 49 as displayed on the temperature setpoint indicator 57. The temperature controller 49 preferably includes a control algorithm such as time proportioning, error proportioning, proportional (P), integral (I), derivative D, proportional-integral-derivative (PID) or the like to compare the actual temperature as measured by the temperature sensor 48 to the setpoint displayed on the setpoint indicator 57, and to output a heating signal 55*a* or a cooling signal 55*b* or neither, depending whether the actual temperature is below, above or within an acceptable tolerance of the setpoint accordingly. In an alternate embodiment, the temperature controller 49 sends an analog signal or a digital communication signal to a heat pump controller (not shown) integral to the heat pump 46. Preferably, the temperature controller 49 controls the temperature between about 68° F. and 75° F. within a tolerance of about ±0.5° F., but is capable of maintaining the temperature in the vessel 12 between 55° F. and 95° F. The temperature controller 49 can work with other temperature scales such as Celsius, Kelvin, and the like, or other process units such as percentage of full scale, numeric counts, millivolts and the like, without departing from the present invention.

Preferably, the temperature controller 49 is a Marine Air Systems Passport II. However, the temperature controller 49 could be other commercially available temperature controllers, process controllers or a custom built controller without departing from the broad inventive scope of the present invention.

Optionally, the environmental control apparatus 40 includes a relative humidity sensor (not shown) electrically connected to a relative humidity indicator/alarm unit (not shown) for displaying the measured relative humidity of the gas inside the pressure vessel 12. It is contemplated that such a relative humidity sensor could also be connected to a relative humidity controller (not shown) for controlling a humidifier, a dehumidifier, a misting device, a desiccant dryer, a refrigerator dryer, a heated air dryer or the like to thereby control the relative humidity within the pressure vessel 12.

Figure 5:
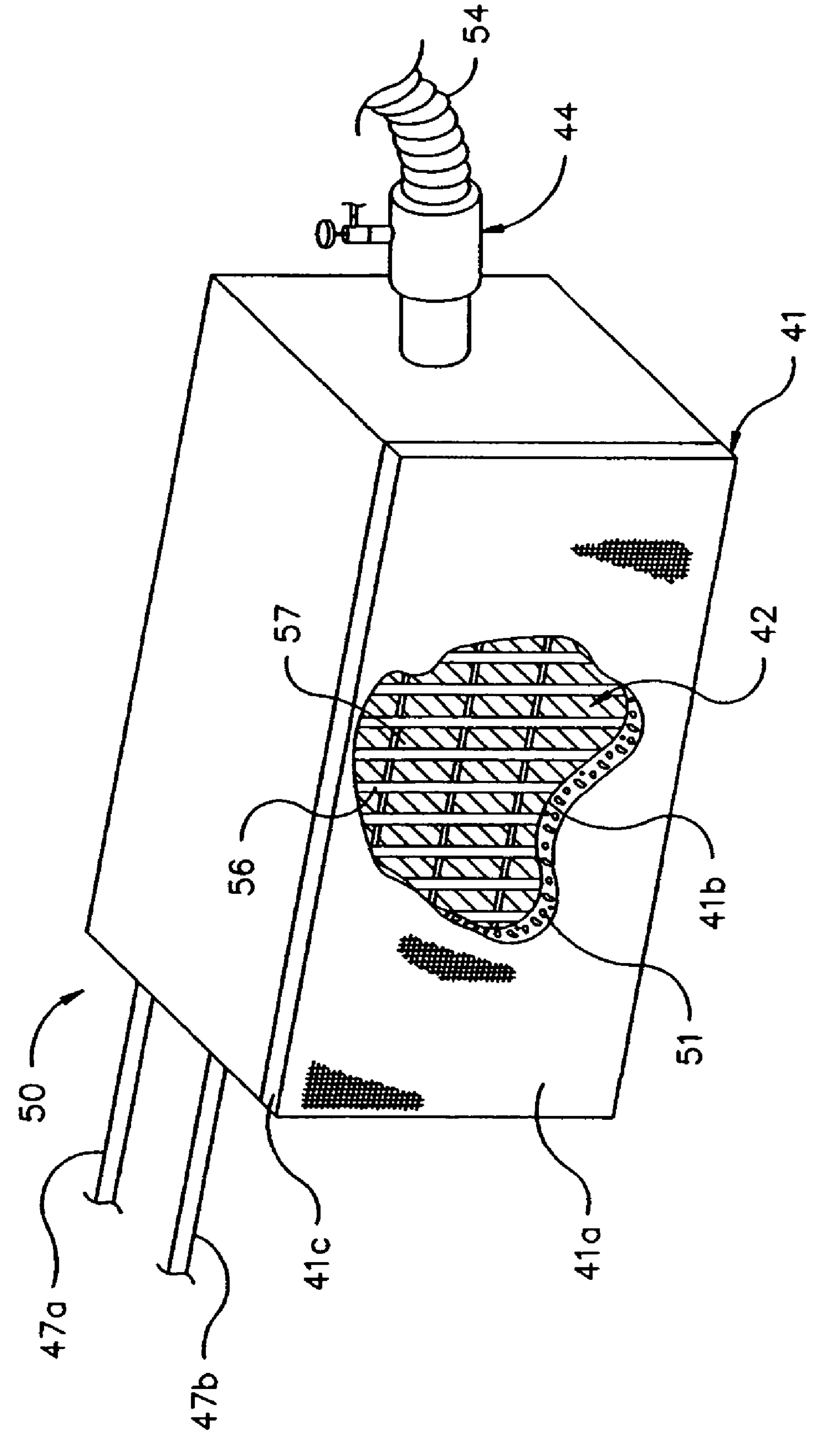
FIG. 5 is a partially broken away perspective view of an exchange controller in accordance with the preferred embodiment.
Figure 6A:
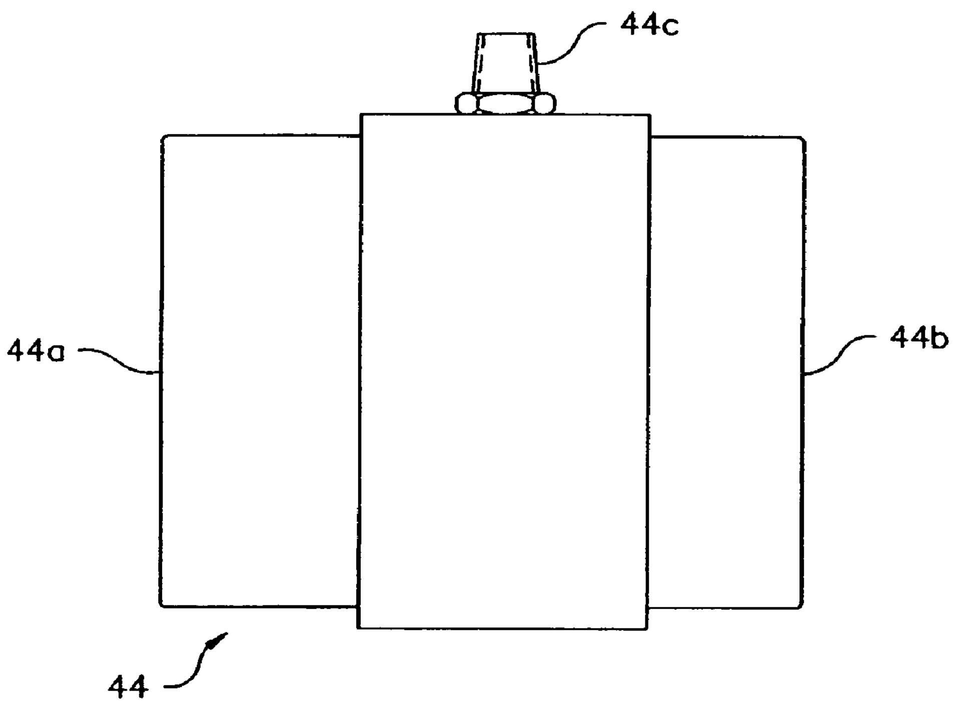
FIG. 6A is a side elevational view of an injection blower in accordance with the preferred embodiment.
Figure 6B:
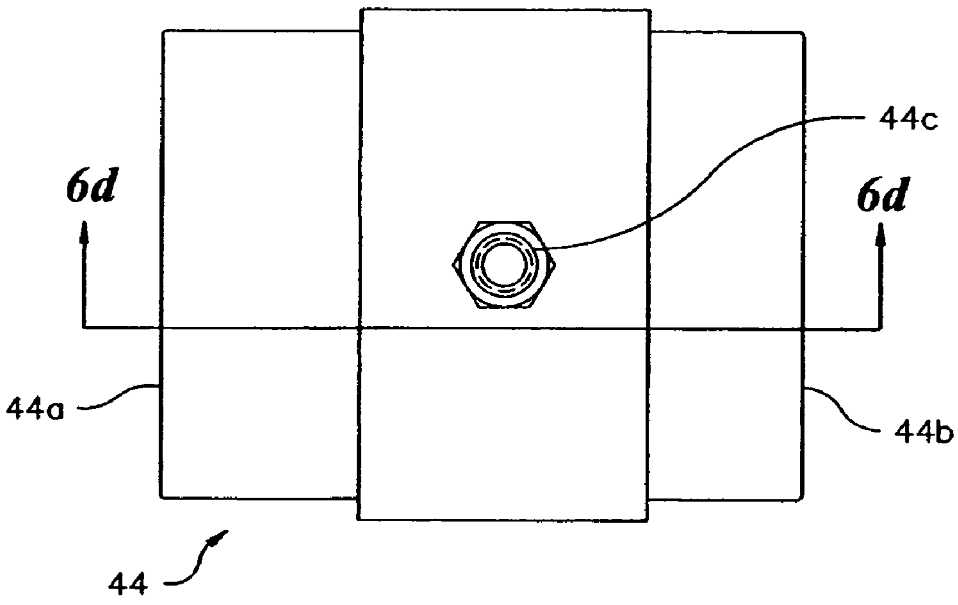
FIG. 6B is a top view of the injection blower shown in FIG. 6A.
Figure 6C:
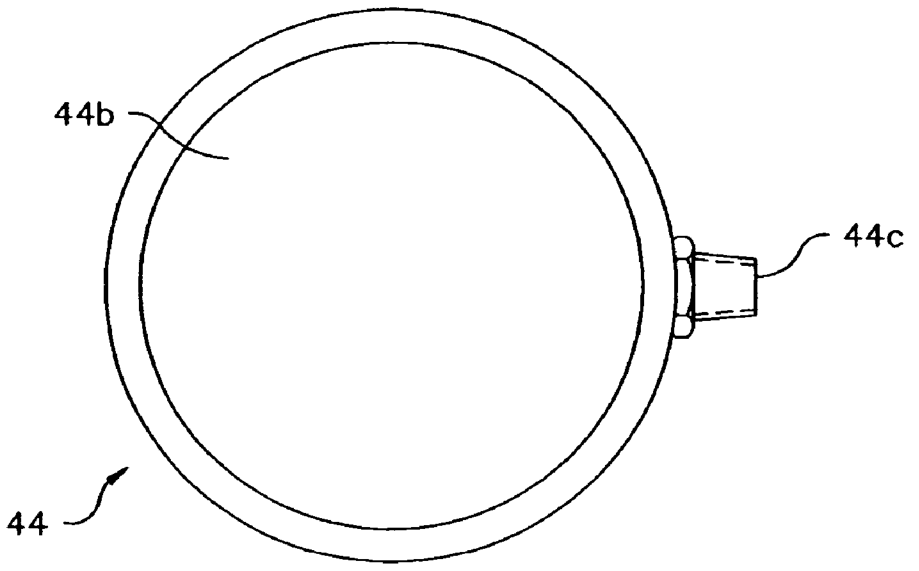
FIG. 6C is an end view of the injection blower shown in FIG. 6A.
Figure 6D:
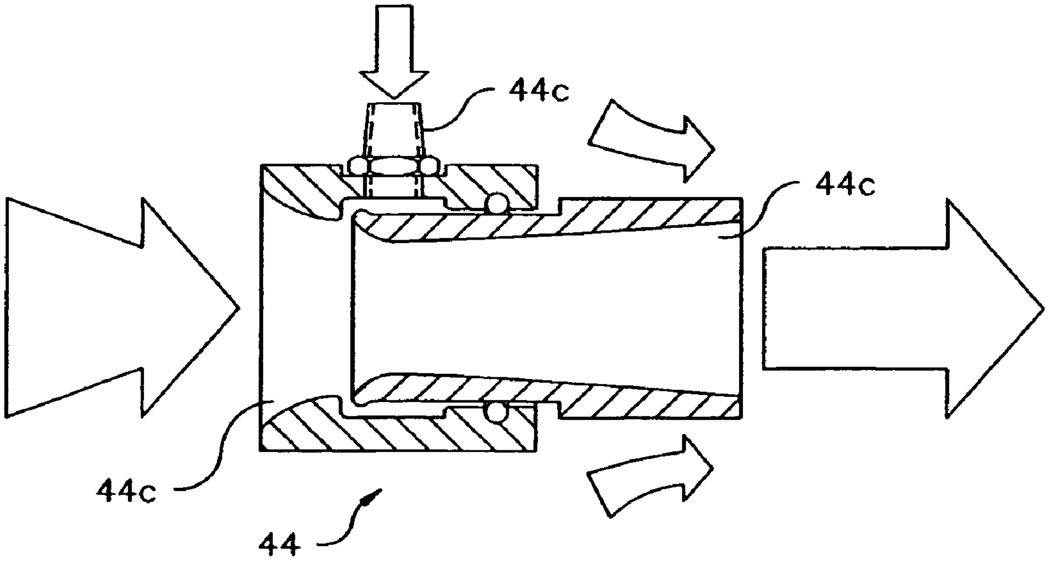
FIG. 6D is a sectional view of the injection blower taken along the line 6D-6D of FIG. 6B.

An exchange enclosure 50 is shown in FIG. 5. The exchange enclosure 50 houses the heat exchanger 42, the scrubber 41 and the blower 44. While the exchange enclosure 50 of the presently preferred embodiment is a rectangularly-shaped, box-like structure, the exchange enclosure 50 may be other shapes or structures. The exchange enclosure 50 is preferably formed of light-gage galvanized aluminum panels, but the exchange enclosure 50 may be formed of other materials of different or varying thickness. Alternatively, the exchange enclosure 50 is a plurality of mounting brackets or angles, such as a pipe-rack, used only to physically support the heat exchanger 42, the scrubber 41 and the blower 44. The exchange enclosure 50 is not critical to the invention and therefore, will not be discussed in greater detail herein.

Preferably, the scrubber 41 of the present invention contains a carbon dioxide adsorbing packing material 51 for removing carbon dioxide from the gas. Preferably, the carbon dioxide adsorbing packing material 51 is substantially formed of sodium calcium hydrate. In the preferred embodiment, the carbon dioxide adsorbing packing material 51 is substantially formed of Sodasorb® as manufactured by Dewey and Almy Chemical Company Corporation, Cambridge, Mass. or its chemical equivalent. The scrubber 41 may contain other carbon dioxide adsorbing packing materials such as sodium hydroxide lime crystals or other carbon dioxide adsorbing filters, resins and the like without departing from the broad inventive scope of the present invention. The scrubber 41 includes a porous inlet panel 41*a* and a porous outlet panel 41*b* retained by a scrubber frame 41*c*. The porous panels 41*a,* 41*b* are preferably a fine-mesh stainless steel screen. However, the porous panels 41*a,* 41*b* may be formed of other materials. The scrubber 41 is preferably a generally rectangularly-shaped box defined by the rectangularly-shaped scrubber frame 41*c;* however, the scrubber 41 may have other shapes and configurations without departing from the present invention. The scrubber frame 41*c* is preferably formed of galvanized aluminum, but the frame can be formed of other materials such as polymeric materials, rubber, wood, stainless steel and the like. The scrubber 41 preferably secures to an open side of the exchange enclosure 50 thereby forming a solitary inlet path for entering gas, as described in greater detail below.

Referring to FIGS. 5 and 6A-6D, the blower 44 of the present invention is an injection-type blower that moves the gas in the interior 12*a* of the vessel 12 by a gas received from a source of pressurized gas. Preferably, the blower 44 receives compressed air (CA) from an outtake 85 of a compressor 80, described in greater detail below. However, the blower 44 may operate from other sources of compressed gas such as bottled gases and the like. The blower 44 has a blower intake 44*a,* a blower discharge 44*b,* and a pressurized gas supply port 44*c* connected to a source of pressurized gas. The pressurized gas being supplied to the pressurized gas supply port 44*c* causes surrounding gas to be drawn through the blower intake 44*a* and out the blower discharge 44*b* by induction. Preferably, the blower intake 44*a* is connected to a cutout in an end panel of the exchanger enclosure 50. When the pressurized gas is supplied to the pressurized gas supply port 44*c* gas is drawn in through the porous inlet panel 41*a* from a lower portion the interior 12*a* of the pressure vessel 12, through the carbon dioxide adsorbing packing material 51, out the porous outlet panel 41*b,* across the heat exchanger 42, into the blower intake 44*a,* out through the blower discharge 44*b* and through a corrugated recirculation tube 54 which discharges the gas at an upper portion of the interior 12*a* of the pressure vessel 12. Alternatively, the blower 44 can be mounted upstream of the heat exchanger 42 and/or the scrubber 41. The ordering of the blower 44, the heat exchanger 42 and the scrubber 41 is not critical to the functionality of the present invention and therefore, the blower 44, the heat exchanger 42 and the scrubber 41 can be arranged in any order so long as gas from the interior 12*a* of the pressure vessel 12 passes through the scrubber 41 and across the heat exchanger 42.

The heat exchanger 42 is preferably a fin 56 and tube 57 configuration similar to that of a conventional radiator or an air conditioner. Heat exchangers are generally well known in the art. Accordingly, a variety of heat exchangers employing coils, tube bundles, plates and the like, or combinations thereof, may be utilized without departing from the broad inventive scope of the present invention.

The hyperbaric oxygen therapy system 10 (shown in FIG. 1) also includes the compressor 80 having an intake 84, compressor motors 86, a receiver tank 82, the outtake 85, and compressor silencers 90. The compressor motors 86 are electrically operated and drive gas-compressing pistons (not shown) which compress gas drawn from the atmosphere through the intake 84 of the compressor 80 and discharged into the receiver tank 82 which provides storage capacity for the compressor 80. The supply voltage for the compressor 80 is between about 100 VAC and 600 VAC at about 50 Hz to 60 Hz, single phase or three phase. Preferably, the supply voltage is about 460 VAC to about 500 VAC at about 60 Hz three phase. The compressed gas is preferably air. The receiver tank 82 stores compressed gas at about 40 pounds per square inch gage (PSIG) to about 149 PSIG. Preferably, compressor pressure switches (not shown) connected to the receiver tank 82 cause the compressor motors 86 to run when the pressure of the compressed gas drops to about 80 PSIG and cause the compressor motors 86 to continue to run until the pressure of the compressed gas in the receiver tank 82 reaches about 125 PSIG. The compressed gas leaves the receiver tank 82 through the outtake 85 of the compressor 80 to pressurize the pressure vessel 12 and to supply the pressurized gas supply port 44*c* of the blower 44. The compressor 80 supplies compressed gas at a rate of about 1 cubic feet per minute (CFM) to about 25 CFM, but preferably at a rate of about 6 CFM to 8 CFM. The compressed gas may be used for additional purposes such as actuating other valves, cylinders, and the like not described in detail herein. The receiver tank 82 may have a drain valve 83 for blowing off accumulated condensation (condensate). The drain valve 83 may be manual or automatically actuated either mechanically or electrically. The intake 84 may have an intake filter (not shown) for trapping debris in the gas before compression. Likewise, the outtake 86 may have an outtake filter or trap (not shown) for trapping excess condensate or other materials prior to use of the compressed gas. The outtake 86 may also have a discharge pressure regulator (not shown) for maintaining a discharge pressure within a predetermined range of pressure. Gas compressors are generally well known in the art and are not critical to the present invention. Accordingly, the gas compressor 80 is not described in greater detail herein.

Referring to FIGS. 8A-8D, each compressor silencer 90 includes a silencer housing 91 having an elongate body 94. The elongate body 94 has an inlet end 94*a* and an outlet end 94*b*. The silencer housing 91 further includes an inlet cap 96 secured to the inlet end 94*a* of the body 94 and an outlet cap 98 secured to the outlet end 94*b* of the body 94. The compressor silencer 90 also includes at least two elongate support rods 102 mounted within the elongate body 94 and extending at least partially between the inlet end 94*a* and the outlet end 94*b* of the body 94. The support rods 102 preferably extend from a threaded coupling (not shown) on a side of the inlet cap 96 facing the inlet end 94*a* of the body 94, through an interior lumen of the body 94 and through the outlet cap 98. The compressor silencer 90 further includes a porous packing material 100 that reduces noise created by the compressor 80. The packing material 100 is located within the elongate body 94 and fills at least part of the volume between the inlet end 94*a* and the outlet end 94*b* of the body 94. Preferably, the packing material 100 extends the entire length of the body 94 and is supported by the inlet cap 96 and the outlet cap 98. Preferably, the packing material 100 is formed of an elongate cylinder of porous material that extends substantially the entire length of the body 94. But, the packing material 100 need not be a continuous structure. The packing material 100 may be shaped in other configurations such as wafers, beads, randomly-shaped pieces and the like without departing from the present invention, The packing material 100 is formed in a manner such that there is enough porosity to allow gas to pass through the packing material 100 without severely restricting the operation of the compressor 80, but also provides adequate sound dampening. Preferably, the packing material 100 is formed of high density polyethylene (HDPE). In the preferred embodiment, the packing material 100 is POREX® as manufactured by Porex Technologies Corp., Fairburn, Ga. However, the packing material 100 may be formed of other materials having similar qualities without departing from the invention.

A pair of retaining nuts 104 attach by mating threads (not shown) to ends 102*a* of the support rods 102 thereby securing the outlet cap 98 to the elongate body 94 and firmly supporting the ends 102*a* of the support rods 102. Other attachment mechanisms for securing the outlet cap 98 to the elongate body 94 and the ends 102*a* of the support rods 102 such as cotter pins, rivets, wire-ties and the like may be utilized without departing from the broad scope of the present invention.

Preferably, there are two compressor silencers 90 wherein one compressor silencer 90 is connected to the intake 84 of the compressor 80 and the other compressor silencer 90 is connected to the outtake 85 of the compressor 80. The inlet cap 96 of the compressor silencer 90 is connected to the outtake 85 of the compressor 80. The outlet cap 96 of the compressor silencer 90 is connected to the intake 84 of the compressor 80. The compressor silencers 90 may be varied in length and/or diameter depending whether they are attached to the intake 84 or the outtake 85 of the compressor 80 and depending on the size of a particular pressure vessel 12.

The hyperbaric oxygen therapy system 10, as shown in FIG. 1, also includes the pressure/ventilation control apparatus 60 includes pressure controlling valve 62 for regulating a flow of pressurized gas into the pressure vessel 12, a pressure sensor 68 having a sensing portion in fluid communication with the gas in the pressurized vessel 12 that outputs a signal representative of a pressure of the gas within the pressure vessel 12, a first or ascent valve 65, a second or ventilation valve 64 that regulates a gas flow out of the pressure vessel 12, and a pressure controller 67 having a programmable pressure profile.

Figure 9:
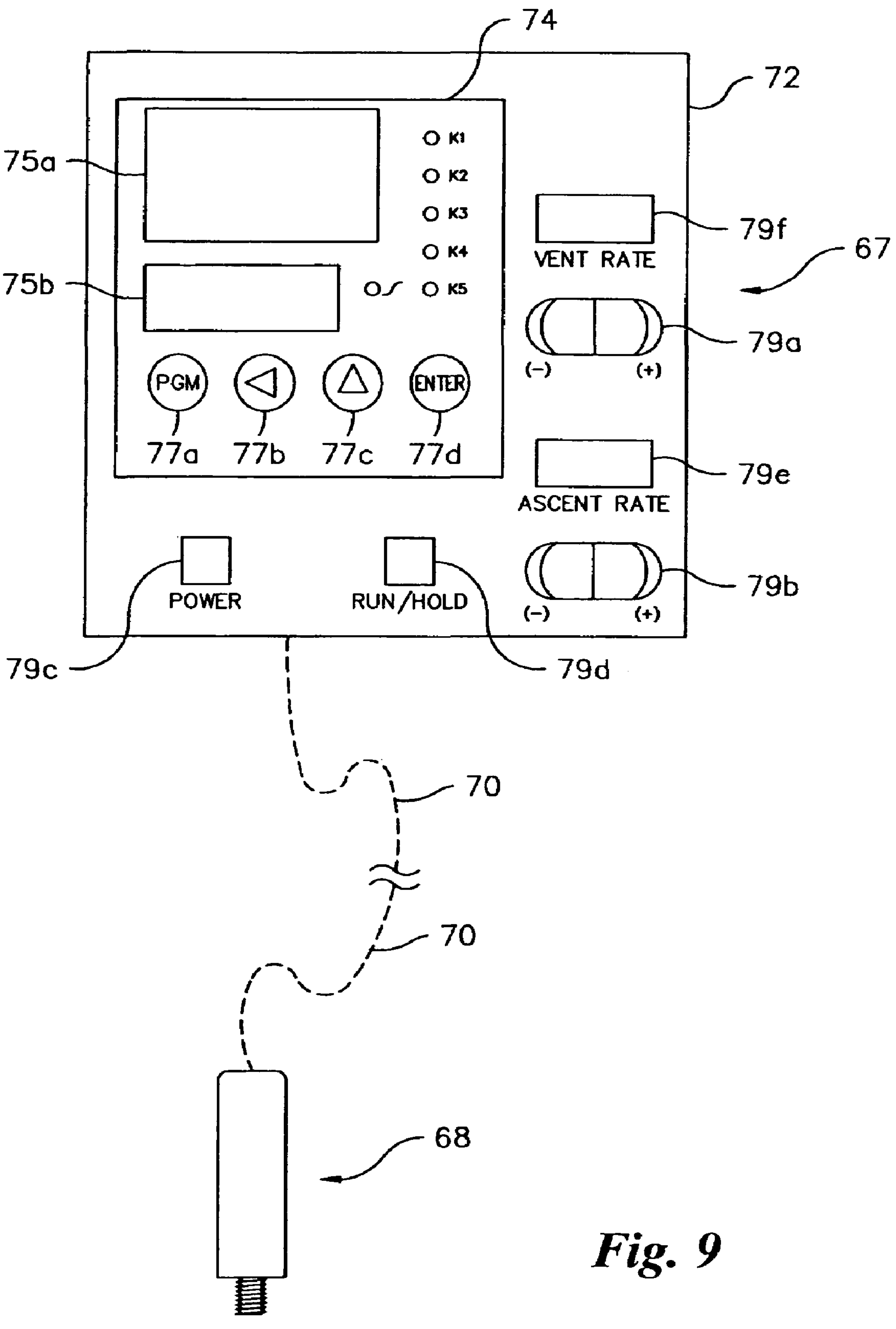
FIG. 9 is a front view of a pressure controller and a pressure sensor in accordance with the preferred embodiment.

Referring to FIG. 9, the pressure sensor 68 provides the signal representative of the pressure of the gas by a pressure signal cable 70. While the pressure sensor 68 is preferably directly connected to or mounted within the pressure vessel 12, the pressure sensor 68 could alternatively be connected to a line or pipe that is connected to the pressure vessel 12 thereby providing fluid communication with the gas in the vessel 12. The pressure sensor 68 may be a piezoresistive-type sensor, a capacitive-type sensor, a strain-gage-type sensor and the like. Pressure sensors are generally well known in the art and therefore, a known pressure sensor capable of measuring pressure of a gas may be utilized without departing from the present invention.

The pressure controller 67 controls the pressure controlling valve 62 to maintain a pressure of the gas in the pressure vessel 12 to within a predetermined range around the programmed pressure profile and controls the ventilation valve 64 to adjust the ventilation flow rate according to the pressure profile. The pressure controller 67 includes a microprocessor-based profile controller 74 in addition to a programmable controller board or PLC 76 (FIG. 1) with associated operator interface switches 79*a*, 79*b*, buttons 79*c*, 79*d* and indicators 79*e*, 79*f*. At least the profile controller 74 and the interface switches 79*a*, 79*b*, buttons 79*c*, 79*d* and indicators 79*e*, 79*f* are mounted in a pressure control mounting plate 72. The profile controller 74 preferably has an actual pressure indicator 75*a*, a current pressure setpoint indicator 75*b*, and programming/display keys 77*a*, 77*b*, 77*c*, 77*d*. An operator can use the programming/display keys 77*a*-77*d* to configure the profile controller according to a sequence of setpoints and ramp-rates. The pressure displayed in the indicators 75*a*, 75*b* can be in units of feet of sea water (fsw), meters of sea water (msw), feet of fresh water (ffw), meters of fresh water (mfw), pounds per square inch (PSI), PSIG, atmospheres (ATM), atmospheres absolute (ATA), kiloPascals (kPa), bar, torr and the like, but preferably the units are in ATA. The indicators 75*a*, 75*b* can display in other units such as percentage of full scale, counts, dimensionless units and the like without departing from the present invention. The profile controller 74 is preferably a dTron 04.1 as manufactured by Jumo Process Control, Inc., Coatesville, Pa. The profile controller 74 may be other commercially available controllers or may be a custom controller using a microprocessor, microcontroller, ASIC or the like. The profile controller 74 compares the actual pressure as measured by the pressure sensor 68 to the current setpoint as displayed on the current pressure setpoint indicator 75*b* and controls a pressure valve output signal 63 using a control algorithm such as PI, PD, or PID and the like. The profile controller 74 preferably has tuning parameters for adjusting a response of the pressure valve output signal 63 based upon the response of the entire pressure/ventilation control apparatus and associated devices.

Preferably, the ventilation valve 64 is actuated to vent the pressure vessel 12 when the pressure is substantially steady. An adjustable flow regulator 69 is connected to the ventilation valve 64, wherein the venting flow rate is regulated according to the adjustment of the adjustable flow regulator 69 during the time that the ventilation valve 64 is actuated (open). The adjustable flow regulator 69 may be a variable area flowmeter, a rotameter, a pilot operated regulator and the like. Preferably, the ascent valve 65 is actuated to vent the pressure vessel 12 when the pressure in the pressure vessel 12 is decreasing. Accordingly, the ascent valve 65 is preferably a larger valve than the ventilation valve 64 or is a similar size as the ventilation valve 64 but has a less restricted flow path (i.e., no flow regulator or a flow regulator that is adjusted to attain higher flow rates). The PLC 76 preferably controls the ventilation valve 64 via a ventilation valve output signal 78 and controls the ascent valve 65 based upon an ascent valve output signal 79.

Preferably, the pressure profile includes a first pressure set point, a second pressure set point, a time rate of change of increasing pressure from the second pressure set point to the first pressure set point, a soak-time at the first pressure where the pressure is substantially steady and a rate of change of decreasing pressure from the first pressure set point to the second pressure set point.

In use, an operator or technician sets a pressure profile using the pressure controller 67, sets a treatment temperature of the gas in the pressure vessel using the temperature controller 49, and sets a first ventilation rate using the adjustable flow regulator 69. The pressure/ventilation control apparatus 60 of the hyperbaric oxygen therapy system 10 performs a treatment cycle in accordance with the pressure profile wherein the pressure is first changed from a first pressure to a second pressure, after which the pressure of the gas is maintained at a substantially steady pressure during which time the gas in the pressure vessel 12 is vented from the pressure vessel 12 at the first ventilation rate, after which the pressure of the gas is decreased and the gas in the pressure vessel 12 is vented at a second rate. During the treatment cycle, the oxygen concentration in the pressure vessel 12 is monitored at a plurality of locations using the oxygen concentration measurement apparatus 20. Concurrently during the treatment cycle, carbon dioxide is removed from the gas and the temperature of the gas is maintained at the treatment temperature using the environmental control apparatus 40. Different pressure profiles may be used to treat different patients or ailments. The pressure profiles may include complex sequences of varying pressure increases and various soak times. The oxygen concentration connected to the breathing line 21 may be varied in accordance with the varying pressures and soak times.

Figure 10B:
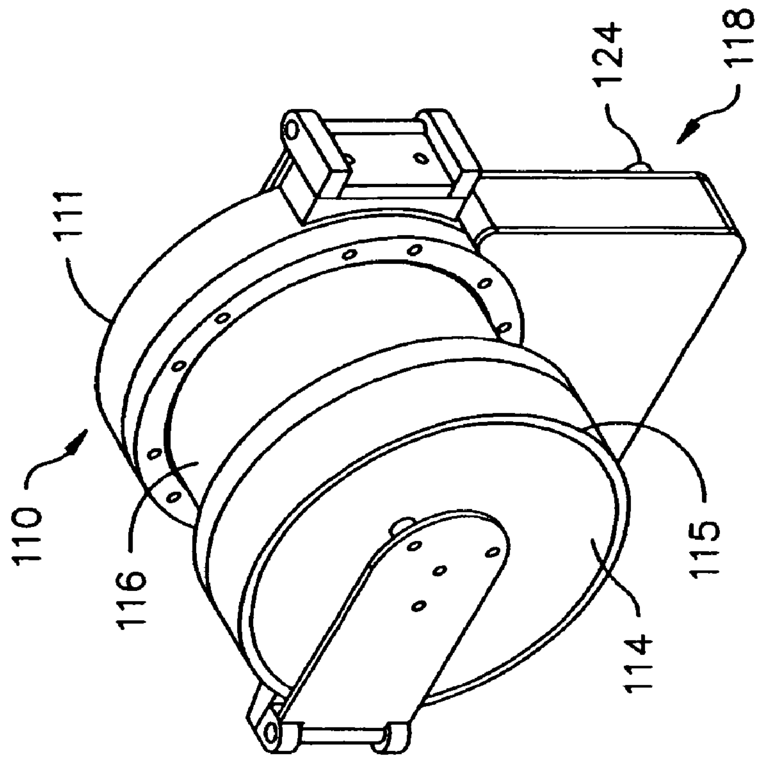
FIG. 10B is a rear perspective view of the airlock of FIG. 10A.
Figure 10A:
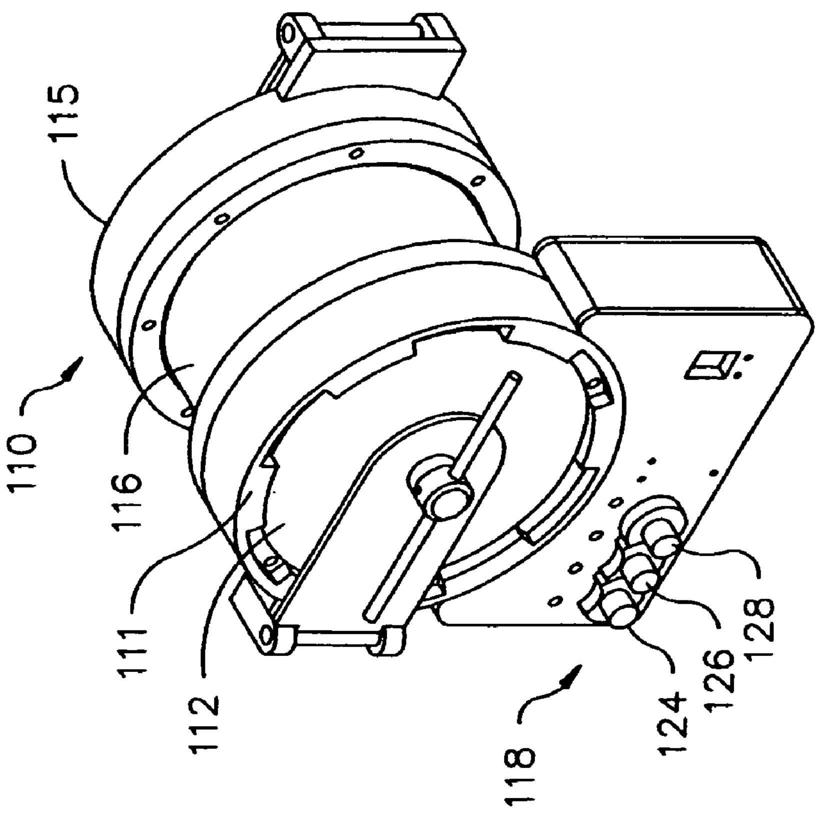
FIG. 10A is a front perspective view of an airlock according to the preferred embodiment.

FIGS. 10A-10B, show an airlock 110 providing access to the pressure vessel 12. The airlock 110 includes an exterior door 112 mounted in an exterior door frame 111, an interior door 114 mounted in an interior door frame 115 and a transfer chamber 116 connecting the exterior door frame 111 and the interior door frame 115.

FIGS. 11A-11D and 12A-12B show a safety mechanism 118 in accordance with the preferred embodiment including a first selector 124 located in the exterior door frame 111 moveable between a first position and a second position and a second selector 126 located in the exterior door frame 111 adjacent to the first selector 124. The second selector 126 is moveable from a first position to a second position only when the first selector 124 is in the second position. The first selector 124 is moveable from the second position to the first position only when the second selector 126 is in the first position. The safety mechanism also includes a third selector 128 moveable from a first position and a second position only when the second selector 126 is in the second position of the second selector 126. The second selector 126 is moveable from the second position to the first position only when the third selector 128 is in the first position of the third selector 128.

Figure 11A:
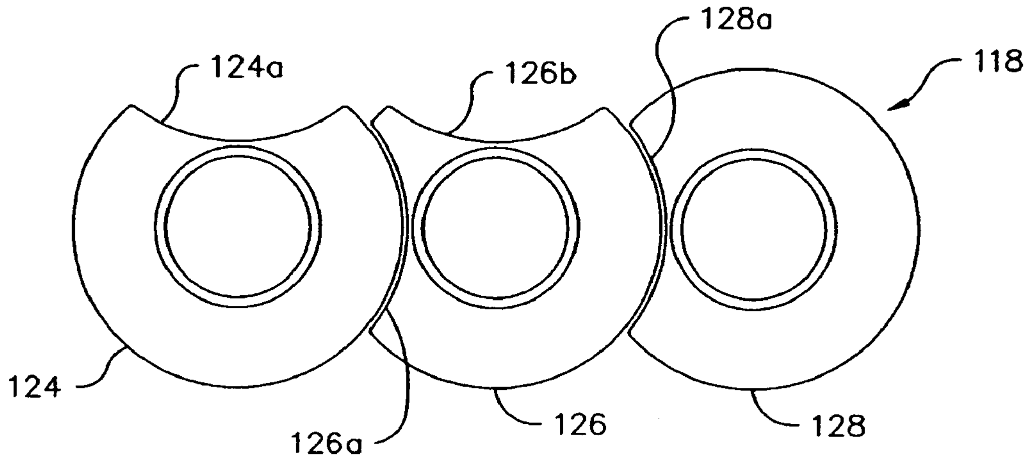
FIG. 11A is a front view of a safety mechanism in accordance with the preferred embodiment showing first, second and third selectors in a first position.
Figure 11B:
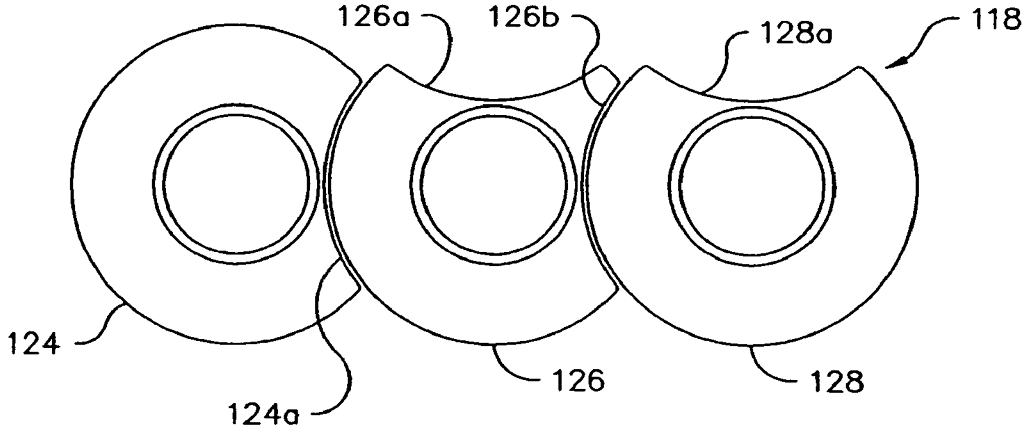
FIG. 11B is a front view of a safety mechanism shown in FIG. 11A showing the first, second and third selectors in a second position.
Figure 11C:
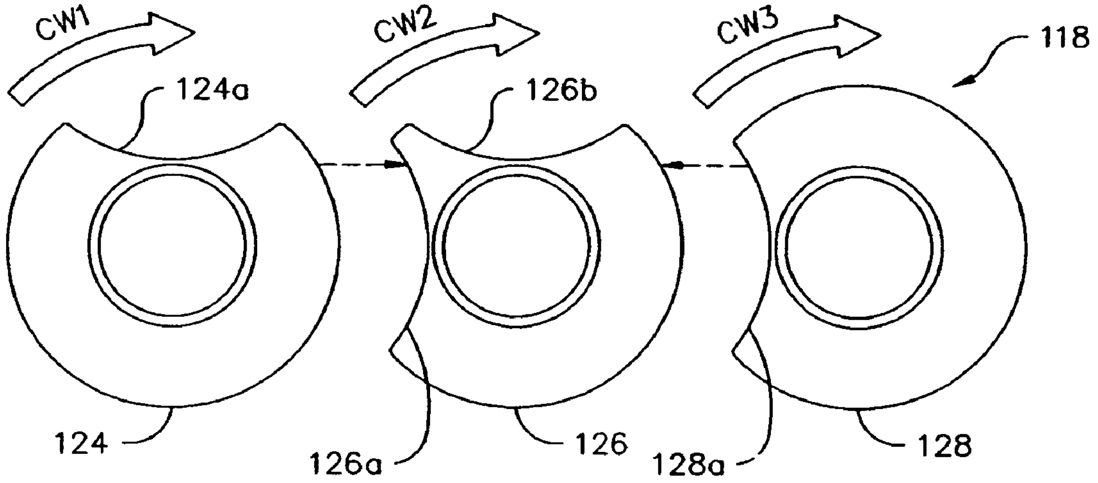
FIG. 11C is a front exploded view of a safety mechanism in accordance with the preferred embodiment showing the first, second and third selectors in the first position.
Figure 11D:
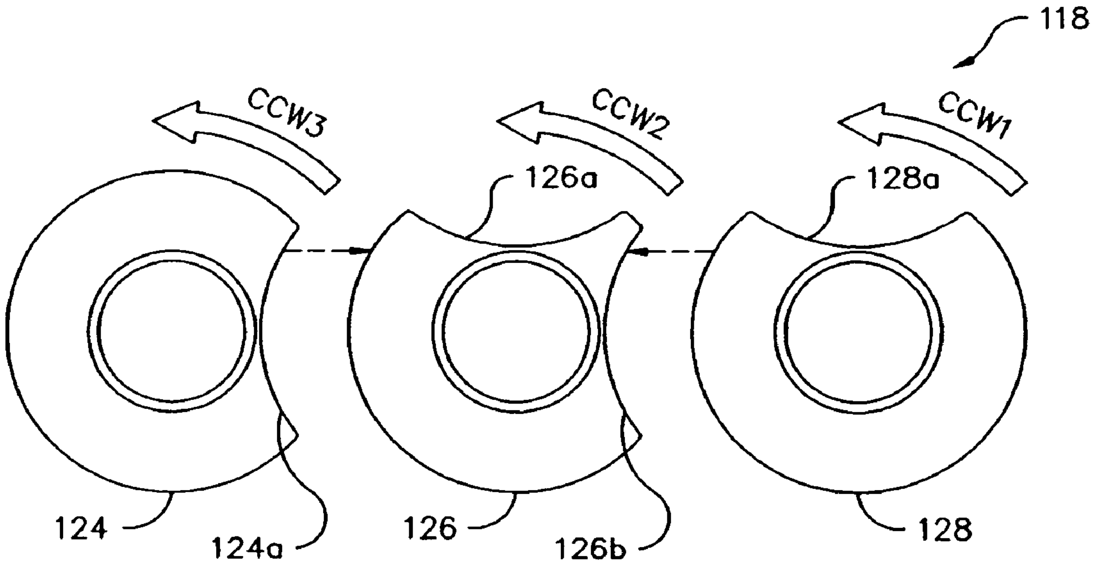

FIG. 11A shows the selectors 124, 126, 128 in the first position. FIG. 11B shows the selectors 124, 126, 128 in the second position. FIG. 11C shows the selectors 124, 126, 128 of FIG. 11A wherein the selectors 124, 126, 128 have been physically separated to demonstrate the structure of the selectors 124, 126, 128. FIG. 11D shows the selectors 124, 126, 128 of FIG. 11B wherein the selectors 124, 126, 128 have been physically separated to demonstrate the structure of the selectors 124, 126, 128. The first selector 124 has a first indentation 124*a* for allowing the second selector 126 to rotate once the first selector 124 is in the second position. The second selector 126 has a first indentation 126*a* for preventing the second selector 126 from rotating until after the first selector 124 has been rotated to the second position and for allowing the first selector 124 to be rotated to the first position after the second selector 126 has been rotated to the first position. The second selector 126 also has a second indentation 126*b* for allowing the third selector 128 to rotate to the second position after the second selector 126 has been rotated to the second position and for preventing the second selector 126 from rotating to the first position until after the third selector 128 has been rotated to the first position. The third selector 128 has a first indentation 128*a* for preventing the third selector 128 from rotating to the second position until the second indentation 126*a* of the second selector 126 permits the third selector 128 to rotate to the second position and for allowing the second selector 126 to rotate to the first position after the third selector 128 has rotated to the first position.

In the presently preferred embodiment as shown in FIG. 11C, the first selector 124 must be rotated in the direction of arrow CW1 before the second selector 126 can be rotated in the direction of arrow CW2. Similarly, the second selector 126 must be rotated in the direction of arrow CW2 before the third selector 128 can be rotated in the direction of arrow CW3. Thus, the first selector 124 is rotated in the direction of CW1, then the second selector 126 is rotated in the direction of CW2, and then the third selector 128 is rotated in the direction of CW3.

In the presently preferred embodiment as shown in FIG. 11D, the third selector 128 must be rotated in the direction of arrow CCW1 before the second selector 126 can be rotated in the direction of CCW2. Similarly, the second selector 126 must be rotated in the direction of arrow CCW2 before the first selector 124 can be rotated in the direction of arrow CCW3. Thus, the third selector 128 is rotated in the direction of arrow CCW1, then the second selector 126 is rotated in the direction of arrow CCW2, and then the first selector 124 is rotated in the direction of arrow CCW3.

Figure 12A:
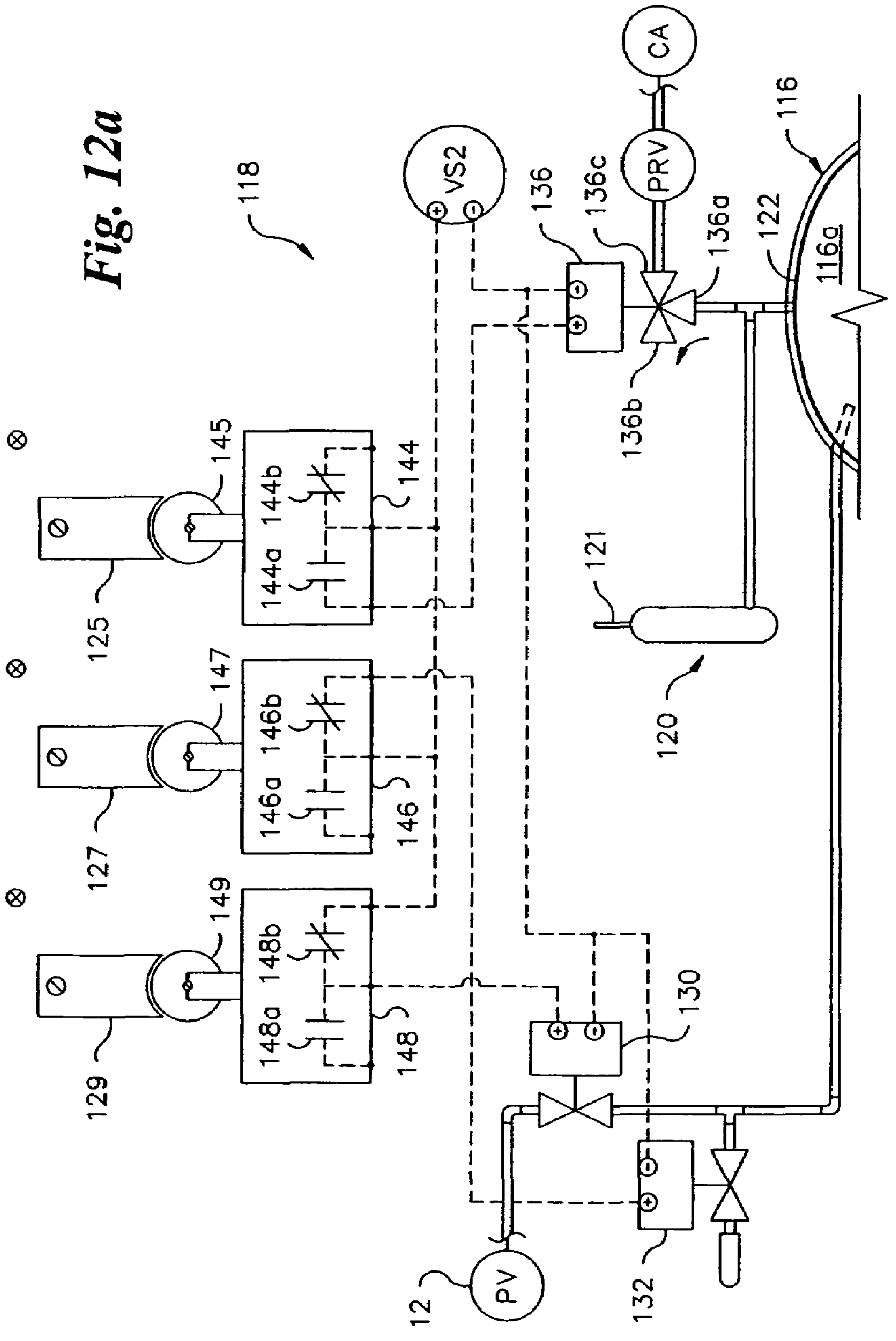
FIG. 12A is a schematic diagram of the safety mechanism with an exterior door in an unlocked state.
Figure 12B:
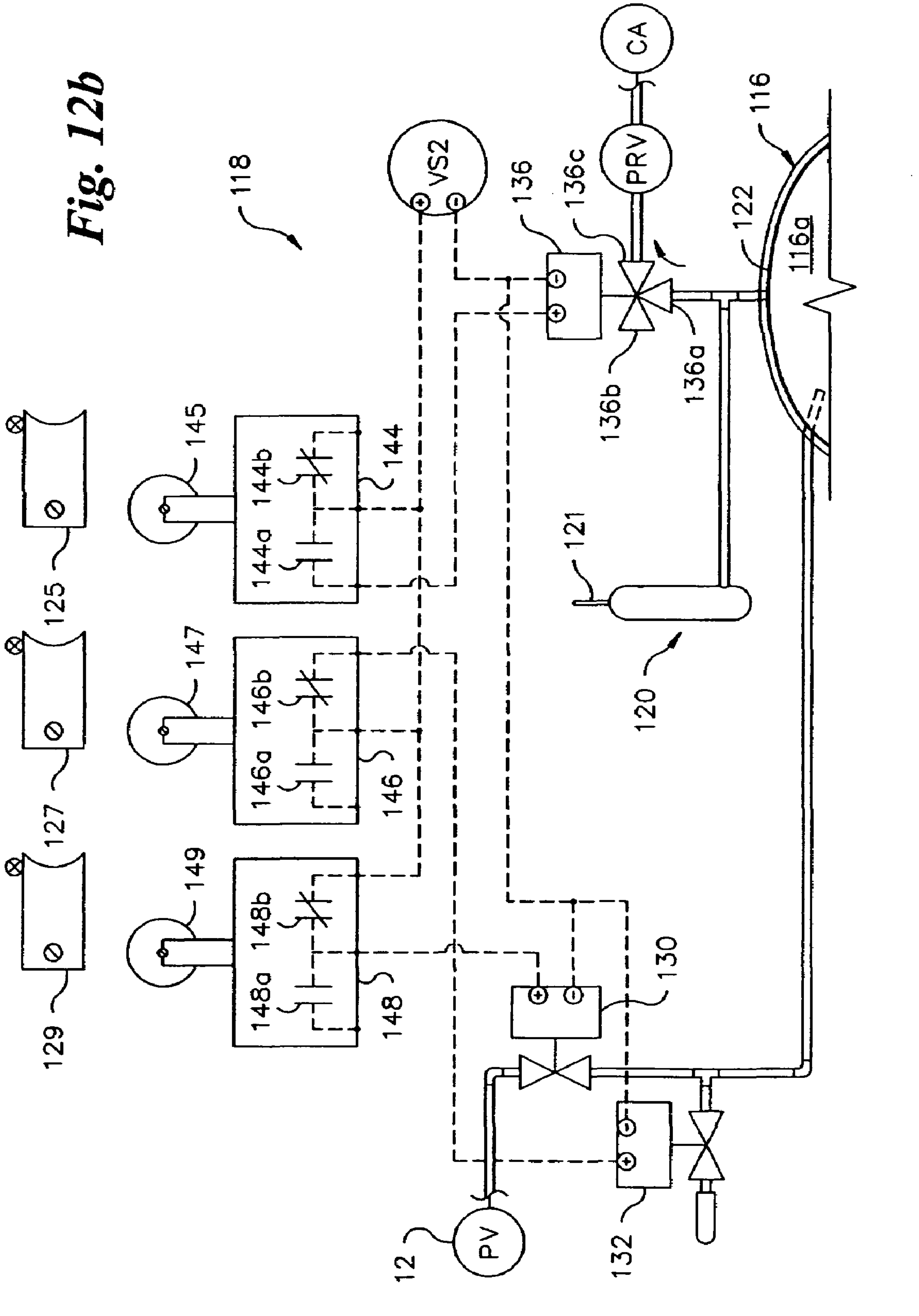
FIG. 12B is a schematic diagram of the safety mechanism with the exterior door in a locked state.

Referring to FIGS. 12A-12B, the preferred embodiment of the safety mechanism 118 also includes a door lock cylinder 120 having a lock pin 121 mounted within the exterior door frame 111 and connected to the first selector 124. The first selector 124 actuates the door lock cylinder 120 into a locking position to lock the exterior door 112 to the exterior door frame 111 when the first selector 124 is in the second position. The safety mechanism also includes a back-seating O-ring or simply an O-ring 122 between a periphery of the exterior door 112 and the exterior door frame 111. The first selector 124 causes the O-ring 122 to be pressurized when the first selector 124 is in the second position thereby sealing the exterior door 112 to the exterior door frame 111.

In the presently preferred embodiment, a first lever 125 is part of, or is mechanically secured to, the first selector 124 such that the first lever 125 moves with the first selector 124. FIG. 12A shows the first lever 125 in a first position, and FIG. 12B shows the first lever 125 in a second position. In the first position, the first lever 125 depresses a first plunger 145 of a first microswitch 144. The first microswitch 144 has a normally open (N.O.) contact 144*a* and a normally closed (N.C.) contact 144*b*. When the first plunger 145 is depressed, the N.O. contact 144*a* closes and the N.C. contact 144*b* opens. Preferably, a three-way supply valve 136 is electrically connected to the N.O. contact 144*a* of the first microswitch 144, and the N.O. contact is electrically connected to a power source VS2. When the first plunger 145 is depressed (FIG. 12A), the N.O. contact 144*a* is closed thereby energizing the three-way supply valve 136 and directing a first supply port 136*a* to a second supply port 136*b* thereby venting the first supply port 136*a* to atmosphere. When the first plunger 145 is released (FIG. 12B), the N.O. contact 144*a* is open thereby de-energizing the three-way supply valve 136 and directing the first supply port 136*a* to a third supply port 136*c* thereby connecting a regulated pressure source to the door lock cylinder 120 and the O-ring 122. The contacts 144*a*, 144*b* and the supply ports 136*a*, 136*b*, 136*c* could be configured differently so long as the door lock cylinder 120 locks the exterior door 112 and the O-ring 122 is pressurized when the first selector 124 is in the second position.

The safety mechanism 118 also includes a chamber vent valve 132 connected to the second selector 126. The chamber vent valve 132 provides fluid communication between an interior 116*a* of the chamber 116 and atmosphere when the second selector 126 is in the first position and prevents fluid communication between the interior 116*a* of the chamber 116 and the atmosphere only when the second selector 126 is in the second position.

In the presently preferred embodiment, a second lever 127 is part of, or is mechanically secured to, the second selector 126 such that the second lever 127 moves with the second selector 126. FIG. 12A shows the second lever 127 in a first position, and FIG. 12B shows the second lever 127 in a second position. In the first position, the second lever 127 depresses a second plunger 147 of a second microswitch 146. The second microswitch 146 has a N.O. contact 146*a* and N.C. contact 146*b*. When the second plunger 147 is depressed, the N.O. contact 146*a* closes and the N.C. contact 146*b* opens. Preferably, the chamber vent valve 132 is electrically connected to the N.C. contact 146*b* of the second microswitch 146, and the N.C. contact 146*b* is electrically connected to the power source VS2. When the second plunger 147 is depressed (FIG. 12A), the N.C. contact 146*b* is opened thereby de-energizing and opening the chamber vent valve 132 which is a N.O.-type valve (i.e., energize to close) and venting the interior 116*a* of the transfer chamber 116 to atmosphere. When the second plunger 147 is released (FIG. 12B), the N.C. contact 146*b* is closed thereby energizing and closing the chamber vent valve 132 and isolating the interior 116*a* of the transfer chamber 116 from atmosphere.

The safety mechanism 118 further includes an interior pressure valve 130 connected to the third selector 128. The interior pressure valve 130 provides fluid communication between the interior 116*a* of the chamber 116 and the interior 12*a* of the pressure vessel 12 only when the third selector 128 is in the second position and prevents fluid communication between the interior 116*a* of the chamber 116 and the interior 12*a* of the pressure vessel 12 when the third selector 128 is in the first position.

In the presently preferred embodiment, a third lever 129 is part of, or is mechanically secured to, the third selector 128 such that the third lever 129 moves with the third selector 128. FIG. 12A shows the third lever 129 in a first position, and FIG. 12B shows the third lever 129 in a second position. In the first position, the third lever 129 depresses a third plunger 149 of a third microswitch 148. The third microswitch 148 has a N.O. contact 148*a* and N.C. contact 148*b*. When the third plunger 149 is depressed, the N.O. contact 148*a* closes and the N.C. contact 148*b* opens. Preferably, the interior pressure valve 130 is electrically connected to the N.C. contact 148*b* of the third microswitch 148, and the N.C. contact 148*b* is electrically connected to the power source VS2. When the third plunger 149 is depressed (FIG. 12A), the N.C. contact 148*b* is opened thereby de-energizing and closing the interior pressure valve 130 which is a N.C.-type valve (i.e., energize to open). When the third plunger 149 is released (FIG. 12B), the N.C. contact 148*b* is closed thereby energizing and opening the interior pressure valve 130 and connecting the interior 116*a* of the transfer chamber 116 to the interior 12*a* of the pressure vessel 12.

One skilled in the art will recognize that the safety mechanism 118 is not limited to the rotary selectors 124, 126, 128. Other types of selectors such as pushbuttons or slide switches could be used. Further, the safety mechanism 118 could rely on electrical as well as mechanical interlocking to ensure that the exterior door 112 is locked/unlocked and sealed/unsealed and the pressure of the transfer chamber 116 is controlled in the correct order to avoid a hazardous condition.

In order to transfer an object from the interior 116*a* of the transfer chamber 116 of the airlock 110 to the pressure vessel 12 attached to the airlock 110 and ensure that the exterior door 112 of the airlock 110 cannot be opened when the interior 116*a* of the transfer chamber 116 of the airlock 110 is pressurized, an operator outside of the pressure vessel 12 closes the exterior door 112 and actuates the first selector 124 from the first position to the second position whereby the first selector 124 causes the exterior door 112 to be locked and sealed. Thereafter, the outside operator actuates the second selector 126 from the first position to the second position thereby closing the chamber vent valve 132 isolating the interior 116*a* of the transfer chamber 116 of the airlock 110 from the atmosphere. Thereafter, the outside operator actuates the third selector 128 from the first position to the second position thereby opening the interior pressure valve 130 connecting the interior 116*a* of the transfer chamber 116 of the airlock 110 to the interior 12*a* of the pressure vessel 12 thereby enabling the interior door 114 between the interior 12*a* of the pressure vessel 12 and the interior 116*a* of the transfer chamber 116 of the airlock 110 to be opened by a user or an operator inside the pressure vessel 12.

In order to transfer an object from the interior 116*a* of the transfer chamber 116 of the airlock 110 attached to the pressure vessel 12 to the atmosphere and ensure that an exterior door 112 of the airlock 110 opening to the atmosphere cannot be opened when the interior 116*a* of the transfer chamber 116 of the airlock 110 is pressurized, a user or an operator inside the pressure vessel 12 closes the interior door 114 between the interior 116*a* of the transfer chamber 116 of the airlock 110 and interior 12*a* the pressure vessel 12. Thereafter, an operator outside of the pressure vessel 12 actuates the third selector 128 from the second position to the first position thereby closing the interior pressure valve 130 isolating the interior 116*a* of the transfer chamber 116 of the airlock 110 from the interior 12*a* of the pressure vessel 12. Thereafter, the outside operator actuates the second selector 128 from the second position to the first position thereby opening the chamber vent valve 132 connecting the interior 116*a* of the transfer chamber 116 of the airlock 110 to the atmosphere. Thereafter, the outside operator actuates the first selector 124 from the second position to the first position whereby the first selector 124 causes the exterior door 112 to be unlocked and unsealed.

As can be seen from the foregoing description, the preferred embodiment comprises an improved method and apparatus for providing hyperbaric oxygen therapy providing lower noise levels, improved automation and an improved method for transferring objects into and out of a pressure vessel through an airlock.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A hyperbaric oxygen therapy system comprising:

a pressure vessel containing an environment gas, the vessel being configured to accommodate a patient;

a first source of pressurized gas;

a second source of pressurized gas; and an injection blower that moves gas into the pressure vessel from the first source of pressurized gas, the injection blower having an inlet fluidly coupled to the first source of pressurized gas, a discharge fluidly coupled to an interior of the pressure vessel and an induction port fluidly coupled to one of the first source of pressurized gas and the second source of pressurized gas, pressurized gas flow applied through the induction port causing pressurized gas to be drawn through the inlet of the injection blower from the first source of pressurized gas.

2. The hyperbaric oxygen therapy system of claim 1, wherein the first source of pressurized gas is bottled oxygen.

3. The hyperbaric oxygen therapy system of claim 1, wherein the second source of pressurized gas is compressed air.

4. The hyperbaric oxygen therapy system of claim 1, further comprising:

an oxygen concentration measurement apparatus that monitors a concentration of oxygen in the environment gas.

5. The hyperbaric oxygen therapy system of claim 1, further comprising:

an environmental control apparatus for controlling the temperature of the gas in the vessel.

6. The hyperbaric oxygen therapy system of claim 1, further comprising:

a pressure/ventilation control apparatus for controlling the pressure of the gas in the vessel.

* * * * *